US007569027B2

(12) United States Patent  (10) Patent No.: US 7,569,027 B2
Uesugi et al.  (45) Date of Patent: Aug. 4, 2009

(54) APPARATUS FOR SUPPLYING GAS AT TWO DIFFERENT PRESSURES

(75) Inventors: Takefumi Uesugi, Tokyo (JP); Daisuke Sano, Tokyo (JP); Atsuhiko Kasahi, Yokohama (JP); Kenji Noda, Tokyo (JP)

(73) Assignee: Olympus Corporation (JP)

( * ) Notice: Subject to any disclaimer, the term of this patent is extended or adjusted under 35 U.S.C. 154(b) by 831 days.

(21) Appl. No.: 11/091,997

(22) Filed: Mar. 29, 2005

(65) Prior Publication Data

US 2005/0217727 A1  Oct. 6, 2005

(30) Foreign Application Priority Data

Mar. 29, 2004  (JP)  ............................. 2004-097126
Mar. 22, 2005  (JP)  ............................. 2005-082545

(51) Int. Cl.
*A61M 37/00*  (2006.01)
(52) U.S. Cl. ....................................................... 604/23
(58) Field of Classification Search ................... 604/23, 604/26, 31
See application file for complete search history.

(56) References Cited

U.S. PATENT DOCUMENTS

| 3,004,777 | A | | 10/1961 | Buinaccorsi |
| 4,619,640 | A | * | 10/1986 | Potolsky et al. ................ 604/7 |
| 5,197,511 | A | | 3/1993 | Kohn et al. |
| 5,246,419 | A | | 9/1993 | Absten |
| 6,299,592 | B1 | * | 10/2001 | Zander ........................ 604/26 |
| 2001/0034506 | A1 | | 10/2001 | Hirschman et al. |
| 2003/0165794 | A1 | * | 9/2003 | Matoba ....................... 433/114 |

FOREIGN PATENT DOCUMENTS

| GB | 2 262 452 A | 6/1993 |
| JP | 08-256972 | 10/1996 |
| JP | 2000-139830 | 5/2000 |
| WO | WO 99/18383 | 4/1999 |

OTHER PUBLICATIONS

Letter from Spanish associate dated Jul. 26, 2005 forwarding European Search Report dated Jul. 19, 2005 to Japanese associate and including discussion thereof.
Search Report dated Jul. 19, 2005 issued by European Patent Office in connection with corresponding application No. 05006809.7—2310 PCT/.
English translation of Abstract for application No. 05006809.7, 2008.

* cited by examiner

*Primary Examiner*—Kevin C Sirmons
*Assistant Examiner*—Elizabeth R Macneill
(74) *Attorney, Agent, or Firm*—Ostrolenk, Faber, LLP

(57) ABSTRACT

A gas supply apparatus is provided and has first and second fittings and first and second tubes. The first fitting is provided to discharge a gas of a first pressure therethrough, while the second fitting is provided to discharge a gas of a second pressure therethrough. The first tube has one end to which a first connector connectable to the first fitting is attached and supplies the first-pressure gas to a first body cavity of a subject. The second tube has one end to which a second connector connectable to the second fitting is attached and supplies the second-pressure gas to a second body cavity of the subject. The apparatus may comprise an erroneous-connection preventing device preventing an erroneous connection including at least one of a connection of the first connector to the second fitting and a further connection of the second connector to the first fitting.

8 Claims, 11 Drawing Sheets

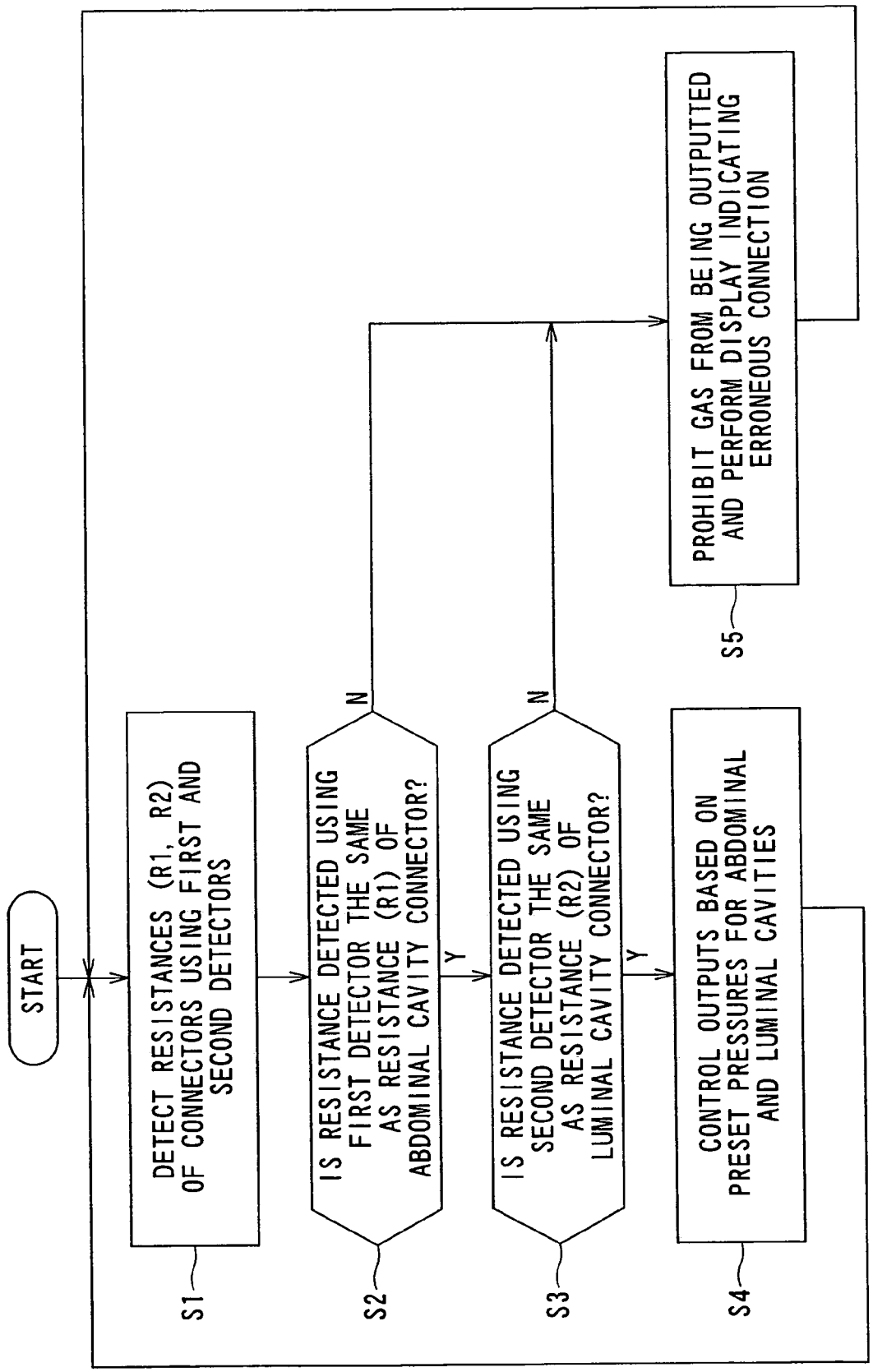

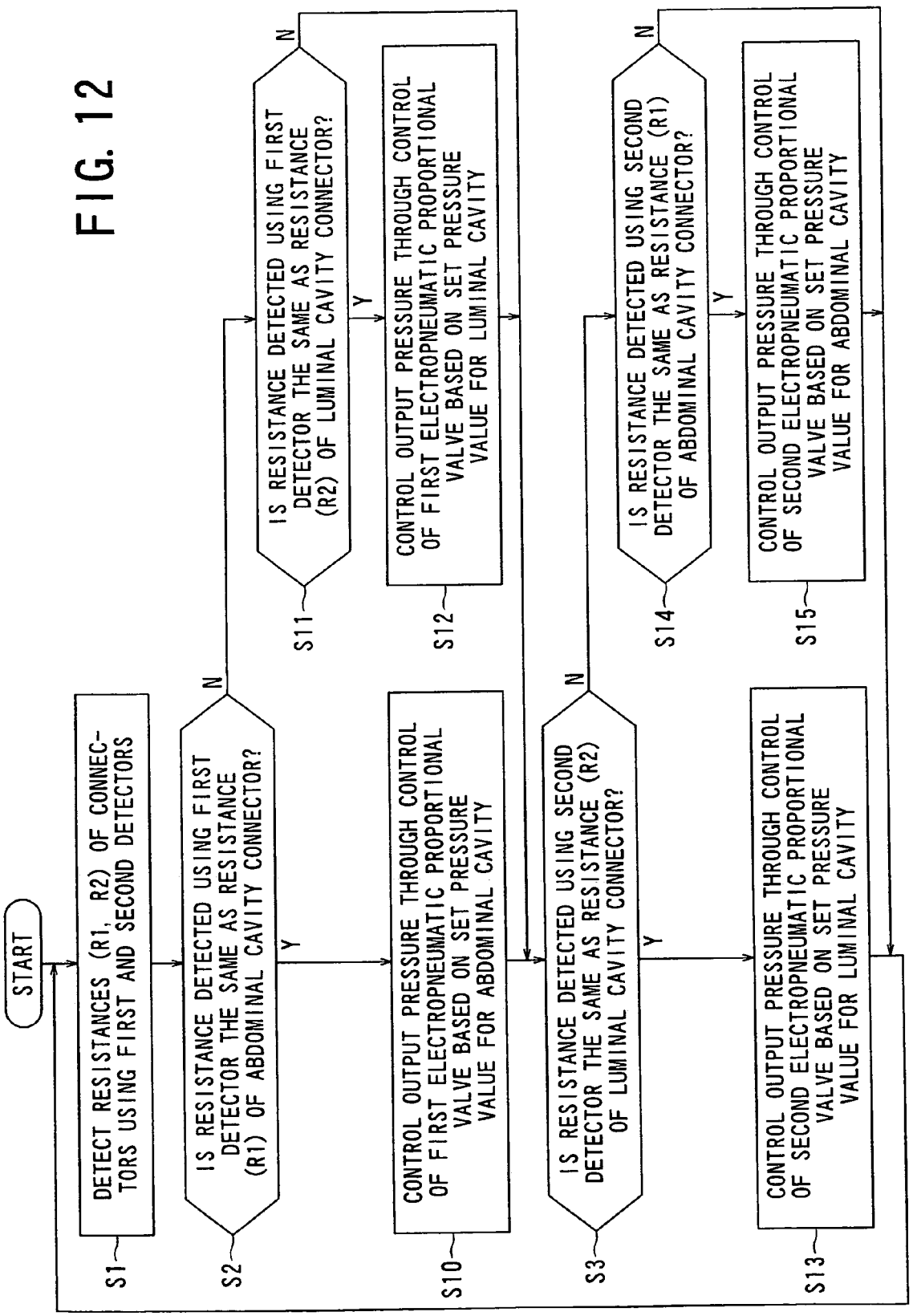

APPARATUS FOR SUPPLYING GAS AT TWO DIFFERENT PRESSURES

CROSS REFERENCE TO RELATED APPLICATIONS

The present application relates to and incorporates by reference Japanese Patent applications No. 2004-97126 filed on Mar. 29, 2004 and No. 2005-82545 filed on Mar. 22, 2005.

BACKGROUND OF THE INVENTION

1. Technical Field of the Invention

The present invention relates to a gas supply apparatus for supplying a predetermined kind of gas (e.g., carbon dioxide gas) to body cavities of a subject to be medically treated, and more particularly, to a gas supply apparatus which supplies gas to different body cavities, such as an abdominal cavity and a luminal cavity, at different pressures, respectively.

2. Related Art

In recent years, laparoscopic surgeries are performed for curative treatment without opening an abdominal cavity, for the purpose of mitigating invasion on a subject to be examined. In a laparoscopic surgery, a first trocar for guiding an endoscope for observation and a second trocar for guiding a treatment tool to a site to be treated, for example, are punctured into an abdomen of a subject. Also, in a laparoscopic surgery, treatment or the like is performed observing both a site to be treated and a treatment tool that has been inserted through an insertion hole of the second trocar, by using an endoscope inserted into an abdominal cavity through an insertion hole of the first trocar.

In such a laparoscopic surgery, an abdominal insufflation apparatus is used for injecting carbon dioxide gas, for example, as an abdominal insufflation gas into an abdominal cavity for purposes of retaining a visual field for the endoscope and a space for manipulating the treatment tool.

For luminal cavities, such as a stomach and a large intestine, an endoscope and a treatment tool as mentioned above are also used for diagnosis and treatment. In effecting medical treatment, including diagnosis and treatment, in luminal cavities, such as a stomach and a large intestine by an endoscopic observation, a gas, such as air as a luminal cavity gas is injected into the luminal cavity for purposes of retaining a visual field for the endoscope and a space for manipulating the treatment tool. Air, which is generally supplied into a luminal cavity by a gas supply pump, may be replaced by carbon dioxide gas.

Recently, a new approach may be taken in a laparoscopic surgery by inserting an endoscope into a luminal cavity to internally and externally specify a site to be treated for effecting treatment. In this case as well, air, for example, may be supplied from an endoscope inserted into a luminal cavity to inflate the luminal cavity.

However, when air is supplied into a luminal cavity as described above, as air is less likely to be absorbed by a living organism, the luminal cavity may possibly remain being inflated and may make it difficult to retain a necessary space for laparoscopic surgery. Accordingly, there has been a need for use of an endoscope $CO_2$ regulator (hereinafter referred to as an ECR), a device for sending a gas such as carbon dioxide gas which is easily absorbed by living organisms, such as a large intestine.

However, arranging conventional surgical equipment for endoscopic surgery by providing an ECR, results in placing a set of the abdominal insufflation apparatus and a $CO_2$ container, separately from a set of the ECR and a $CO_2$ container. This results in increasing variety of pieces of peripheral medical equipment, which are to be accommodated in a plurality of carts, making movement a bothersome labor.

In the prior art equipment described above, two pieces of equipment, i.e. an abdominal insufflation apparatus and an ECR, have to be separately provided, which arises problems of cumbersome and complicated preparation and of spatial inefficiency. Further, when pieces of equipment are separately set up, erroneous connections tend to occur, e.g., connecting a luminal cavity tube to a supply fitting of an abdominal insufflation apparatus, or connecting an abdominal cavity tube to a supply fitting of an ECR.

SUMMARY OF THE INVENTION

The present invention has been made in light of the circumstances described above, and has as its object to provide a gas supply apparatus which enables correct and prompt connection of tubes to a fitting for supplying an abdominal cavity gas and a fitting for supplying a luminal cavity gas, whereby the gas can be correctly supplied.

One aspect of the present invention provides a gas supply apparatus comprising a first fitting through which a gas of a first pressure is discharged; a second fitting through which a gas of a second pressure is discharged; a first tube having one end to which a first connector connectable to the first fitting is attached and supplying the gas of the first pressure to a first body cavity of a subject to be medically treated; and a second tube having one end to which a second connector connectable to the second fitting is attached and supplying the gas of the second pressure to a second body cavity of the subject.

Favorably, there may be provided an erroneous-connection preventing device for preventing erroneous connection, i.e. connecting the first connector to the second fitting, and connecting the second connector to the first fitting.

More favorably, there may be provided: a single gas source for supplying a gas having the first and the second pressures; and a gas supply unit that controls pressure of the gas supplied from the gas source so as to supply the first pressure gas and the second pressure gas to the first and the second fittings, respectively.

In this connection, there may be further provided: for example, a sensor for detecting information on connecting state between the first connector and the first fitting, and between the second connector and the second fitting; a device for judging whether or not connection has been correctly made between the first connector and the first fitting, and between the second connector and the second fitting, based on the information from the sensor; and a gas supply control unit for controlling supply of the first pressure gas and the second pressure gas from the gas supply unit to the first and the second fittings, respectively, based on the results of judgment made by the judging device.

Another aspect of the present invention provides a method for managing connection of conduits in a gas supply apparatus comprising steps of: detecting a state of connection of a first conduit which is connected to a first fitting for discharging a gas having a first pressure, and a state of connection of a second conduit which is connected to a second fitting for discharging a gas having a second pressure; judging whether or not the first connector has been correctly connected to the first fitting, and whether or not the second connector has been correctly connected to the second fitting; giving a command to supply the first pressure gas to the first fitting upon judgment of correct connection as having made between the first connector and the first fitting and giving a command to stop supply of the first pressure gas to the first fitting upon judgment of erroneous connection as having made between the first connector and the first fitting; and giving a command to supply the second pressure gas to the second fitting upon judgment of correct connection as having made between the second connector and the second fitting and giving a command to stop supply of the second pressure gas to the second fitting upon judgment of erroneous connection as having made between the second connector and the second fitting.

BRIEF DESCRIPTION OF THE DRAWINGS

In the appended drawings:

FIG. 11 is a flowchart generally illustrating processes for making judgment of erroneous connection of a tube and for controlling gas supply based on the judgment, which are executed by a controller, according to the third embodiment; and FIG. 12 is a flowchart generally illustrating processes for making judgment of erroneous connection of a tube and for controlling gas supply based on the judgment, which are executed by a controller, according to a fourth embodiment of the present invention.

DETAILED DESCRIPTION OF THE PREFERRED EMBODIMENTS

Embodiments of the present invention will now be described below with reference to the appended drawings.

First Embodiment

Referring to FIGS. 1 to 6, a first embodiment of a gas supply apparatus according to the present invention is described.

Figure 1:
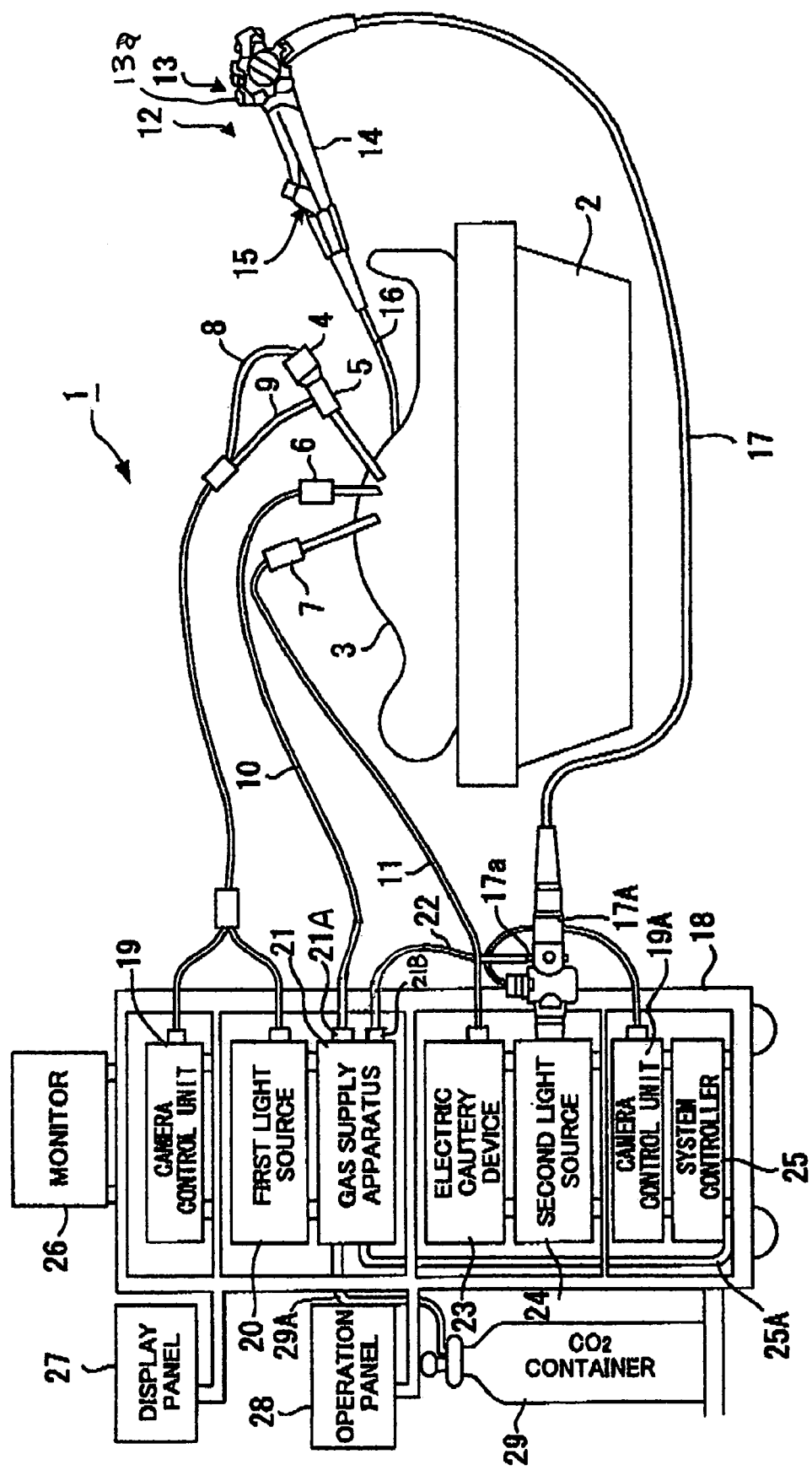
FIG. 1 is a schematic diagram illustrating an endoscopic system including a first embodiment of a gas supply apparatus of the present invention.

FIG. 1 shows an endoscopic system 1 to which the present embodiment of the gas supply apparatus according to the present invention is applied. As shown, the endoscopic system 1 has an endoscope 5 for performing endoscopy in an abdominal cavity of a subject 3 lying on an operating table 2, with the endoscope 5 mounting a TV camera head 4 incorporating an imaging device.

As shown, a guide tube (trocar) 6 for performing abdominal insufflation by supplying carbon dioxide gas for retaining a visual field for the endoscope 5, and a guide tube (trocar) 7 for inserting an electric cautery probe (not shown) for electrically performing cautery, are punctured into the abdominal cavity of the subject 3.

A signal cable 8 is connected to the TV camera head 4, and a light guide cable 9 is connected to the endoscope 5. An abdominal insufflation tube (hereinafter referred to as an abdominal cavity tube) 10 is connected to the abdominal insufflation guide tube 6, and a signal cable 11 is connected to the electric cautery probe (not shown) which is inserted into the electric cautery guide tube 7.

The signal cable 8 and the light guide cable 9 are, respectively, connected to a camera control unit (hereinafter referred to as a CCU) 19 and a first light source device 20 which are both loaded on a trolley 18. The abdominal cavity tube 10 is connected to a gas supply apparatus 21 serving as an abdominal insufflation apparatus, which is loaded on the trolley 18. Further, the signal cable 11 is connected to an electric cautery device 23 loaded on the trolley 18.

The endoscopic system 1 incorporating the present embodiment comprises an endoscope 12 for performing endoscopy in a luminal cavity, such as a large intestine of the subject 3. The endoscope 12 is arranged such that a gas, such as carbon dioxide gas supplied through a gas supply conduit (not shown) in a universal code 17 can be supplied from a tip of an insert 16, by pressing down a gas supply button 13a provided at an operating part 13 which is located at a rear end side of a handle 14.

The universal code 17 comprises therein, although not shown, a signal cable, a light guide and the gas supply conduit, and is connected to a second light source device 24 loaded on the trolley 18 through a connector part 17A. It is arranges such that the connector part 17A has a carbon dioxide gas supply port 17a to which a luminal cavity tube 22 from the gas supply apparatus is connected and that carbon dioxide gas is supplied by the gas supply apparatus 21 through the carbonic gas supply port 17a.

Loaded on the trolley 18 are the CCU 19 for processing signals for the imaging device, the first light source device 20 for providing illumination to the endoscope 5, the gas supply apparatus 21 for supplying a gas (carbon dioxide gas) for use in an abdominal cavity and a luminal cavity, the electric cautery device 23 for feeding high-frequency power for enabling cautery, and the second light source device 24 for providing illumination to the endoscope 12. The trolley 18 also carries thereon, a system controller 25 for performing general control, a CCU (camera control unit) 19A which is connected to the second light source device 24 and used for the endoscope 12, a VTR (not shown) for recording video signals from the CCUs 19 and 19A, a monitor 26 for displaying the video signals, which are obtained from the CCUs 19 and 19A via the system controller 25, in the form of images, a carbon dioxide gas container ($CO_2$ container) 29 for supplying carbon dioxide gas to the gas supply apparatus 21 through a high pressure gas tube 29A.

Further, a display panel 27 for performing display and a panel 28 for performing operation are attached to the trolley 18.

The individual pieces of the medical equipment, such as the CCUs 19 and 19A are connected to the system controller 25 through communication cables, not shown. The system controller 25 may be operated through the operation panel 28 of touch panel type or a remote controller, not shown. Further, indication for the system controller 25 is performed through the operation panel 28 or the display panel 27.

The CCU 19 effects signal processing to the image signals from the endoscope 5 and supplies video signals based on the image signals to the system controller 25, the monitor 26 and the VTR (not shown).

The CCU 19A effects signal processing to the image signals from the endoscope 12 and supplies video signals based on the image signals to the system controller 25 and the VTR (not shown).

The first light source device 20 serves as a light source device for providing illumination through a light guide in the light guide cable 9 to an illumination optical system provided at the endoscope 5. The second light source device 24 serves as a light source device for providing illumination through a light guide in the universal code 17 to an illumination optical system provided at the endoscope 12.

The gas supply apparatus 21, whose internal configuration is described later, is used for retaining a visual field for the endoscope 5 by supplying carbon dioxide gas into an abdominal cavity, for example, of a subject through the abdominal insufflation guide tube 6 connected thereto, and for retaining a visual field for the endoscope 12 by supplying carbon dioxide gas into a luminal cavity, for example, of a subject through the tip of the insert 16 of the endoscope 12 connected thereto.

Figure 5:
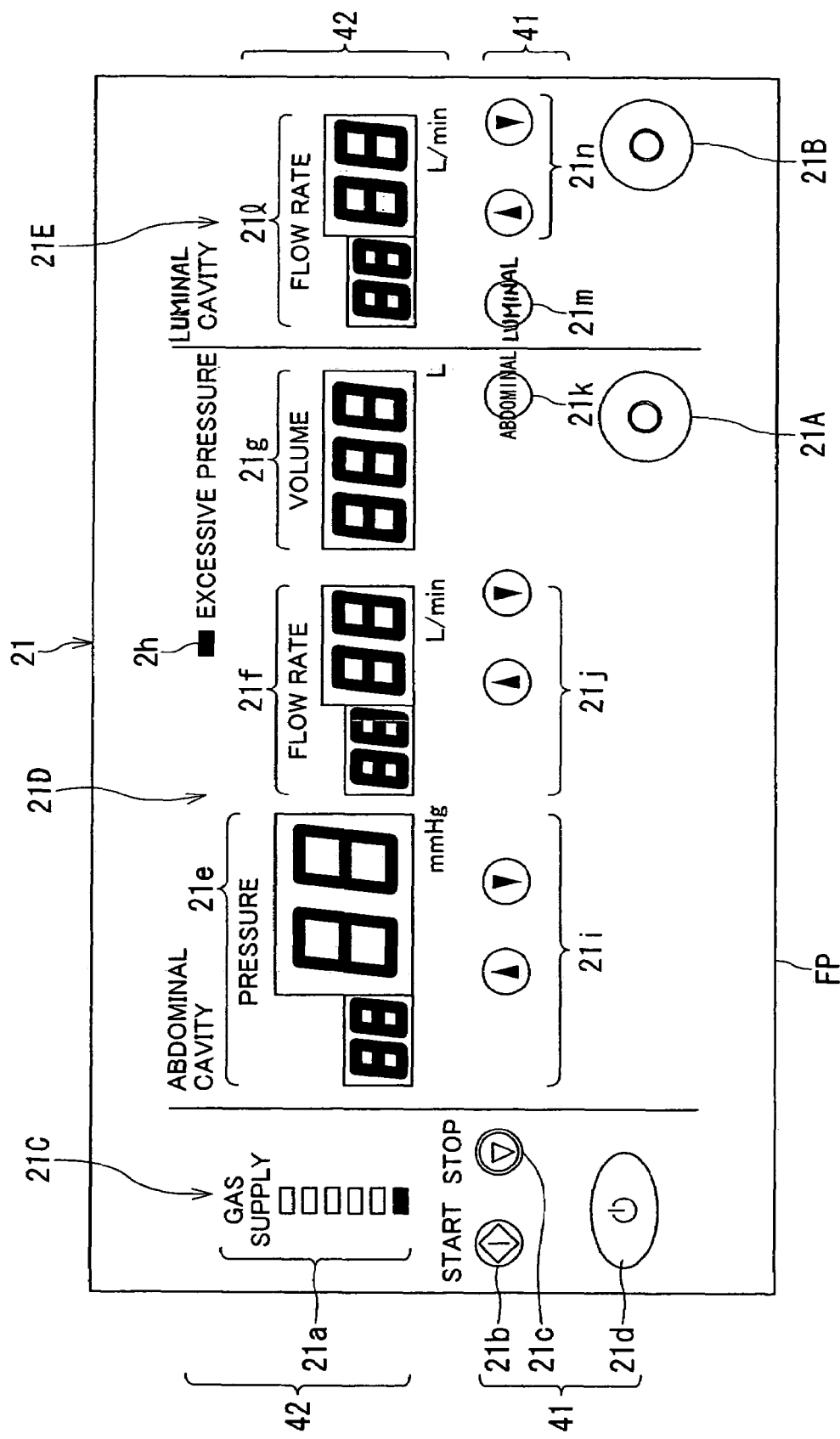
FIG. 5 is an explanatory diagram illustrating a front panel including a preset operation part and a display part.

A supply fitting 21A for abdominal cavity to which the abdominal cavity tube 10 is connected, and a supply fitting 21B for luminal cavity to which the luminal cavity tube 22 from the carbon dioxide gas supply port 17a is connected, are provided at a front panel FP of the gas supply apparatus 21 (see FIG. 5).

The electric cautery device 23 serves as a surgical treatment tool for use in electro-thermal cutting process, for example, at an abnormal site within an abdominal area of a subject, and as a high-frequency output device for outputting a high-frequency current to the surgical treatment tool.

In the system controller 25 are provided an operation signal receiver for receiving a signal from the operation panel 28 and a preset operation part 41 (see FIG. 2), as will be described hereinafter, for the gas supply apparatus 21, an operation driver for transmitting information necessary for the operation panel 28 and for indication at a display 42 (see FIG. 2) for the gas supply apparatus 21.

The system controller 25 is electrically connected to a communication part, not shown, for performing communication with the pieces of medical equipment loaded on the trolley 18. The communication part is so arranged as to be connected to the CCUs 19 and 19A, the first light source device 20, the gas supply apparatus 21, the electric cautery device 23, the second light source device 24, and the VTR, not shown, through communication cables to enable two-way communication with these pieces of medical equipment. It should be noted that FIG. 1 shows an arrangement wherein the gas supply apparatus 21 is connected to the system controller 25 through a connector cable 25A.

In addition, the system controller 25 comprises therein a video signal processor (not shown), which is configured such that image signals from the CCUs 19 and 19A may be processed to produce video signals for transmission to the monitor 26.

The monitor 26 displays the video information, i.e. endoscopic images supplied from the system controller 25.

A configuration of the gas supply apparatus 21 is described below with reference FIG. 2.

Figure 2:
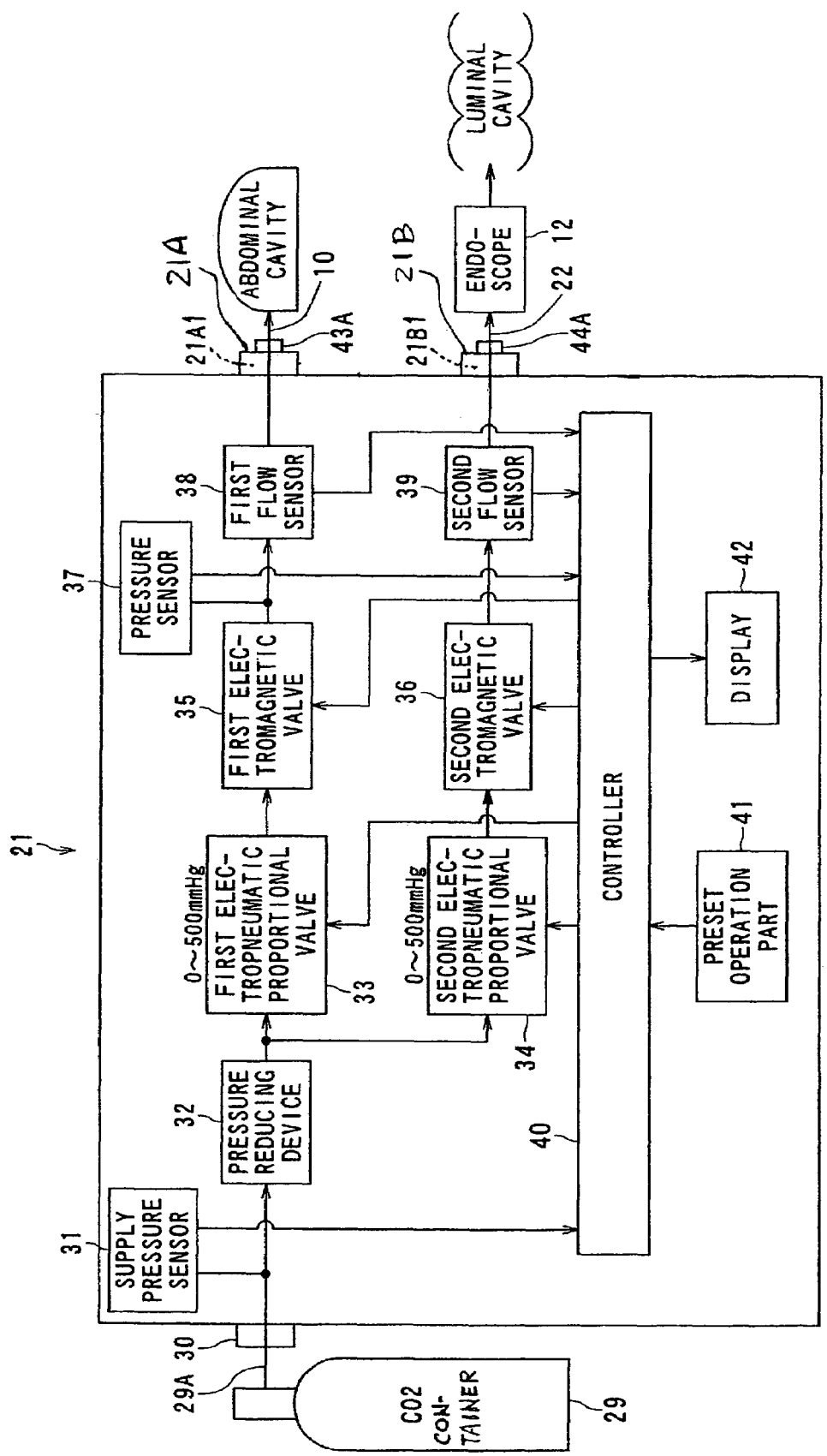
FIG. 2 is a block diagram illustrating a configuration of a gas supply apparatus of the first embodiment.

As shown in FIG. 2, the gas supply apparatus 21 comprises a high-pressure fitting 30, a supply pressure sensor 31, a pressure reducing device 32, a first and second electropneumatic proportional valves 33 and 34, a first and a second electromagnetic valves 35 and 36, a pressure sensor 37, a first and a second flow sensors 38 and 39, a controller 40, the preset operation part 41, the display 42, the abdominal cavity supply fitting 21A having a first detector 21A1, and a luminal cavity supply fitting 21B having a second detector 21B1.

The carbon dioxide gas container 29 and the gas supply apparatus 21 are linked through the high-pressure tube 29A with one end of which being connected to the high-pressure fitting 30 provided at the gas supply apparatus 21.

The signal cable 25A extending from the system controller 25 is adapted to be detachably attached to an electric connector, not shown, of the gas supply apparatus 21 so as to be electrically connected to the controller 40 therein.

The other end (connector part) of the abdominal cavity tube 10 is adapted to be detachably attached to the abdominal cavity supply fitting 21A which is provided at the gas supply apparatus 21. Also, the other end (connector part) of the luminal cavity tube 22 is adapted to be detachably attached to the luminal cavity supply fitting 21B which is provided at the gas supply apparatus 21.

Liquid carbon dioxide stored in the carbon dioxide gas container 29 is gasified and led to the pressure reducing device 32 through an internal conduit inside the gas supply apparatus 21. The carbon dioxide gas, after its pressure being reduced to a predetermined level by the pressure reducing device 32, is led to the internal conduit which is formed into two systems, so that the pressure is adjusted by the first and the second electropneumatic proportional valves 33 and 34 in the systems to the levels suitable for use in the abdominal cavity and the luminal cavity, respectively.

The carbon dioxide gas for abdominal cavity which has been adjusted by the first electropneumatic proportional valve 33 is so arranged to be led into an abdominal cavity through the first electromagnetic valve 35, the first flow sensor 38, the abdominal cavity supply fitting 21A, the abdominal cavity tube 10, and a channel (gas supply conduit, not shown) provided in the abdominal insufflation guide tube 6.

The carbon dioxide gas for the luminal cavity which has been adjusted by the second electropneumatic proportional valve 34 is so arranged to be led into a luminal cavity through the second electromagnetic valve 36, the second flow sensor 39, the luminal cavity supply fitting 21B, the luminal cavity tube 22, the connector part 17A, the universal code 17, and a channel (gas supply conduit, not shown) provided in the endoscope 12.

The supply pressure sensor 31 measures the pressure of the carbon dioxide gas supplied from the carbon dioxide gas container 29 to output the measurement results to the controller 40. The pressure reducing device 32 reduces the pressure of the carbon dioxide gas supplied from the carbon dioxide gas container 29 to a predetermined level for supply to the first electropneumatic proportional valve 33 and the second electropneumatic proportional valve 34.

Pressure control by the first and the second electropneumatic proportional valves 33 and 34 is enabled by the controller 40. Specifically, these valves adjust the pressure, which has been reduced by the pressure reducing device 32, based on a control signal from the controller 40 so as to fall within a predetermined range.

For example, the first and the second electropneumatic proportional valves 33 and 34 can reduce the pressure of the carbon dioxide gas, which has been reduced by the pressure reducing device 32, based on a control signal from the controller 40, so as to fall within a range of 0-500 mmHg.

It should be noted that a range of a gas supply pressure suitable for an abdominal cavity may desirably be about 0-80 mmHg, and that a suitable range of a gas supply flow rate may desirably be about 0.1-35 L/min. Also, a range of a gas supply pressure suitable for a luminal cavity may desirably be about 0-500 mmHg, and that a suitable range of a gas supply flow rate may desirably be about 1-3 L/min.

The first and the second electromagnetic valves 35 and 36 are the valves whose opening and closing can be controlled by the controller 40. Specifically, these valves are switched from an open state to a closed state, or vice versa, in response to a control signal from the controller 40.

The pressure sensor 37 measures the pressure in an abdominal cavity when the first electromagnetic valve 35 is closed, and outputs the results of the measurement to the controller 40.

The first flow sensor 38 measures the flow rate of carbon dioxide gas that flows in the internal conduit passing through the first electromagnetic valve 35, and outputs the results of the measurement to the controller 40. The second flow sensor 39 measures the flow rate of carbon dioxide gas that flows in the internal conduit passing through the second electromagnetic valve 36, and outputs the results of the measurement to the controller 40.

Although not shown, an exhaust valve may be provided between the first electromagnetic valve 35 and the first flow sensor 38. When a measured value of the pressure sensor 37 exceeds a set pressure value of an abdominal cavity, the exhaust valve is adapted to be open in response to a signal from the controller 40 so that the pressure in the abdominal cavity is decreased, thereby allowing the carbon dioxide gas in the abdominal cavity to be discharged in the atmosphere. A similar pressure sensor and an exhaust valve may be provided on the side of an internal conduit for luminal cavity (i.e. between the second electromagnetic valve 36 and the second flow sensor 39).

The preset operation part 41, which is described hereinafter, is connected to the controller 40, so that the controller 40 can execute various controls in response to operation signals from the preset operation part 41. The configuration of the front panel FP comprising the preset operation part 41 and the display 42 will be described later.

Figure 3:
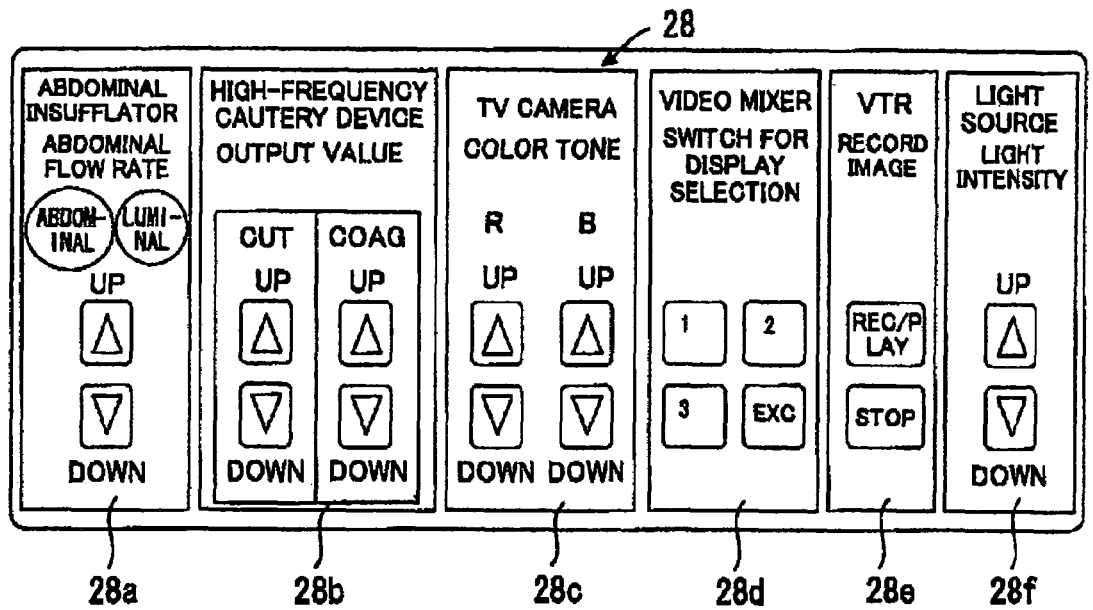
FIG. 3 is an explanatory diagram illustrating an operation panel of a gas supply apparatus.

FIG. 3 shows an exemplary configuration of the operation panel 28 shown in FIG. 1.

As shown in FIG. 3, the operation panel 28 is provided with a preset operation button 28a for adjusting abdominal insufflation flow for an abdominal or luminal cavity caused by the gas supply apparatus (abdominal insufflation apparatus) 21, an operation button 28b for adjusting an output of the electric cautery device (high-frequency combustion device) 23, an operation button 28c for adjusting color tone of the CCUs 19 and 19A, an operation button 28d for instructing change of display of video information to be displayed on the monitor 26, an operation button 28e for instructing to stop recording of the VTR, and an operation button 28f for adjusting quantity of light of the first light source device 20 and the second light source device 24.

Figure 4:
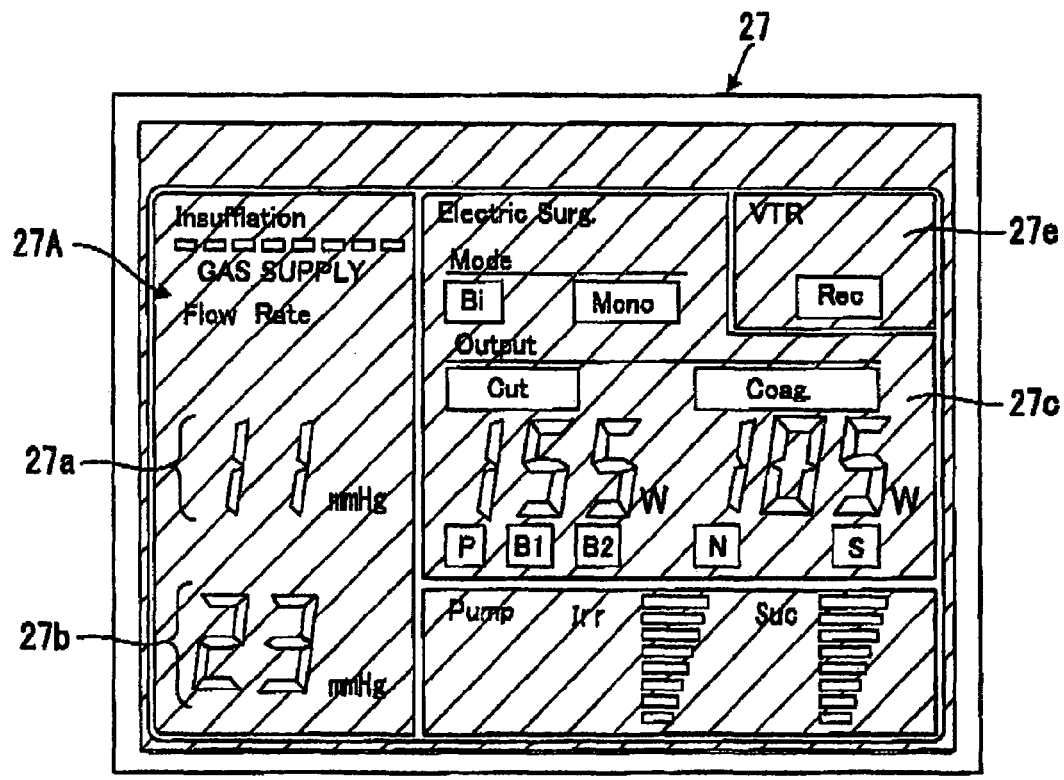
FIG. 4 is an explanatory diagram illustrating a display panel of a gas supply apparatus.

FIG. 4 shows an example of the display panel 27 shown in FIG. 1.

As shown in FIG. 4, the display panel 27 is adapted to display, on display areas 27A (27a, 27b), 27c, 27d and 27e of its display screen, setting and operational conditions with respect to the functions of the gas supply apparatus 21, the electric cautery device 23, a water supply/suction pump (not shown), the VTR (not shown), respectively, for example, whose communication is controlled by the system controller 25. Note that the display area 27A indicates the setting/operational conditions for the gas supply apparatus 21, and includes the display area 27a for internal pressure of a luminal cavity and the display area 27b for internal pressure of an abdominal cavity, as well as a display area for residual quantity of carbon dioxide gas, and a display area for flow rate.

Next, an exemplary configuration of the preset operation part 41 and the display 42 provided at the front panel FP of the gas supply apparatus 21 is described below with reference to FIG. 5.

As shown in FIG. 5, the preset operation part 41 and the display 42 are provided at the front panel FP of the gas supply apparatus 21.

The preset operation part 41 and the display 42 are partitioned into a preset display 21C for preset, operation and display for the carbon dioxide container 29, a preset display 21D for preset, operation and display for an abdominal cavity, and a preset display 21E for preset, operation and display for a luminal cavity. The abdominal cavity supply fitting 21A is provided at a lower side of the preset display 21D, and the luminal cavity supply fitting 21B is provided at a lower side of the preset display 21E. With such disposition and configuration, an operator can easily operate and easily view the gas supply apparatus 21.

In the preset display 21C, there are provided a residual gas quantity display 21a which is included in the display 42, a gas supply start button 21b, a gas supply stop button 21c and a power switch 21d which are included in the preset operation part 41.

In the preset display 21D, there are provided a display 21e for internal pressure of an abdominal cavity, a flow rate display 21*f*, a total gas supply display 21*g* and a pressure warning lamp 2*h* which are included in the display 42, and a preset button 21*i* for internal pressure of an abdominal cavity, a preset button 21*j* for gas supply flow rate and an instruction button 21*k* for an abdominal cavity which are included in the preset operation part 41.

In the preset display 21E, there are provided a display 21*l* for luminal cavity flow rate which is included in the display 42, and an instruction button 21*m* for a luminal cavity and a preset button 21*n* for gas supply flow rate which are included in the preset operation part 41.

The power switch 21*d* switches on and off a power source of the gas supply apparatus 21. The gas supply start button 21*b* is a button for instructing to start gas supply. The gas supply stop button 21*c* serves as a switch for switching from a gas supplying state to a gas supply stopped state.

Each of the preset button 21*i* for internal pressure of an abdominal cavity and the preset button 21*j* for supply gas flow rate has two operational buttons. It is configured such that proper operation of these buttons allows variation in a preset value in a gradually increasing manner or a gradually decreasing manner.

The residual gas quantity display 21*a* indicates a residual quantity of carbon dioxide gas in the carbon dioxide gas container 29. The display 21*e* for internal pressure of an abdominal cavity has two displays, right and left, with the right display indicating a value based on the measurement by the pressure sensor 37, and with the left display indicating, for example, a preset pressure which has been input through the preset button 21*i* for internal pressure of an abdominal cavity.

The flow rate display 21*f* has two displays, right and left, with the right display indicating, for example, a value based on the measurement by the first flow sensor 38, and with the left display indicating a preset flow rate which has been input through the preset button 21*j* for gas supply flow rate.

The total gas supply display 21*g* indicates a total gas quantity which has been obtained through an arithmetic operation by the controller 40 based on the measurement of the first flow sensor 38. When a value measured by the pressure sensor 37 becomes higher, by a predetermined pressure, than a preset value of an abdominal cavity internal pressure, the pressure warning lamp 2*h* gives warning accordingly by varying the state of the lamp from, for example, an off-state to a flickering state or to a red light emitting state in response to a control signal from the controller 40.

The abdominal cavity instruction button 21*k* serves as an instruction button for selecting a mode for the gas supply apparatus 21 to supply carbon dioxide gas into an abdominal cavity. A gas supply mode for an abdominal cavity is adapted to be selected by operating the button.

The luminal cavity flow rate display 21*l* has two displays, right and left, with the right display indicating a value based on the measurement by the flow sensor 39, and with the left display indicating a preset flow rate which has been input through an operation of the supply gas flow rate preset button 21*n*.

The luminal cavity instruction button 21*m* serves as an instruction button for selecting a mode for the gas supply apparatus 21 to supply carbon dioxide gas into a luminal cavity. A gas supply mode for a luminal cavity is adapted to be selected by operating the button.

The supply gas flow rate preset button 21*n* has two operational buttons for presetting a flow rate of carbon dioxide gas when it is supplied into a luminal cavity by the gas supply apparatus 21. Proper operation of these buttons allows variation of a preset value in a gradually increasing manner or in a gradually decreasing manner.

Note that a pressure warning lamp for a luminal cavity, similar to the pressure warning lamp 2*h* may be provided at the preset display 21E for a luminal cavity.

Further, the present embodiment is configured such that when both of the abdominal cavity instruction button 21*k* and the luminal cavity instruction button 21*m* are operated together, a gas supply mode for an abdominal cavity and a gas supply mode for a luminal cavity may be simultaneously performed.

The gas supply apparatus 21 of the present embodiment has two gas supply fittings, i.e. the abdominal cavity supply fitting 21A and the luminal cavity supply fitting 21B, with the configuration wherein a abdominal insufflation apparatus and an ECR are integrated as described hereinbefore. Accordingly, in case of providing such two gas supply fittings 21A and 21B for an abdominal cavity and a luminal cavity, respectively, it is necessary to prevent erroneous connection so that carbon dioxide gas is supplied to each of the gas supply fittings with a right gas supply pressure.

Therefore, the gas supply apparatus 21 of the present embodiment undergoes improvements in the abdominal cavity supply fitting 21A and the luminal cavity supply fitting 21B in order to prevent erroneous connection. An example of such a configuration is described with reference to FIGS. 6A, 6B and 6C.

In the gas supply apparatus 21 of the present embodiment, carbon dioxide gas having a pressure suitable for an abdominal cavity should be supplied to the abdominal cavity supply fitting 21A under the control of the controller 40 over the first electropneumatic proportional valve 33, and carbon dioxide having a pressure suitable for a luminal cavity should be supplied to the luminal cavity supply fitting 21B under the control of the controller 40 over the second electropneumatic proportional valve 34.

Figure 6A:
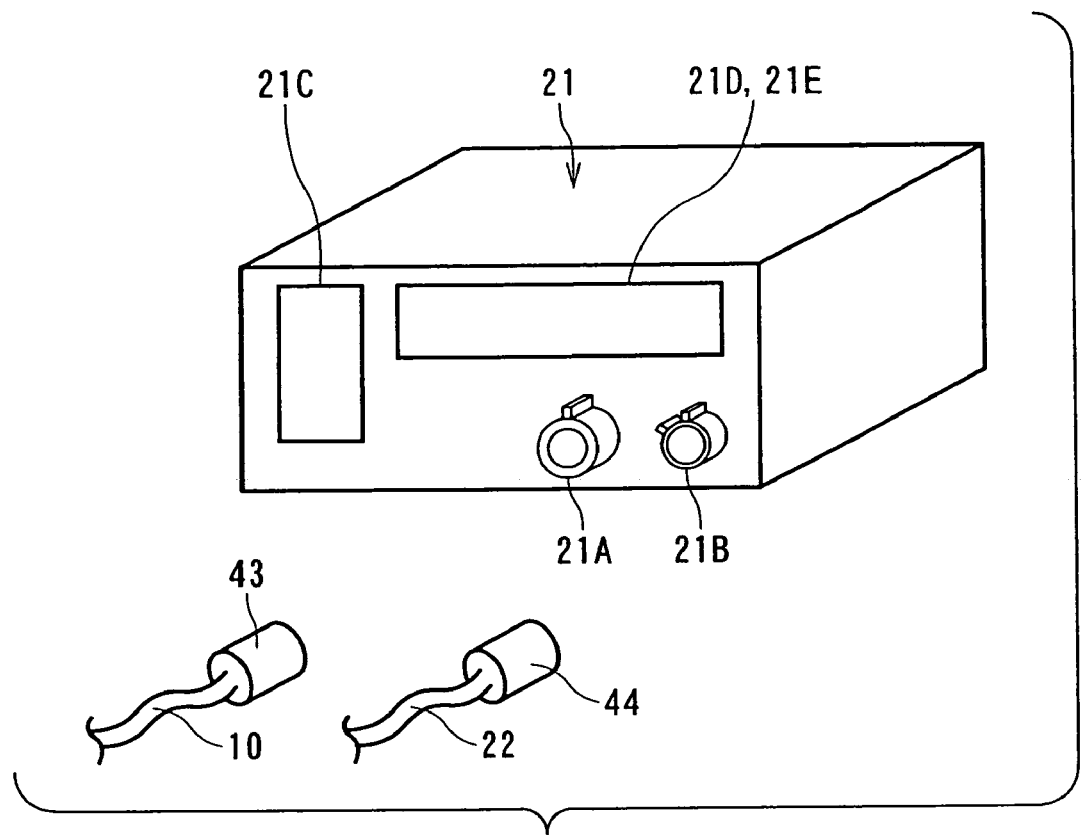
FIG. 6A is a perspective view of a front panel of a gas supply apparatus mounting gas supply fittings, and an abdominal cavity tube and a luminal cavity tube to be connected to the gas supply fittings, respectively.

As shown in FIG. 6A, the gas supply apparatus 21 of the present embodiment is provided with the abdominal cavity supply fitting 21A and the luminal cavity supply fitting 21B having pieces of means for preventing erroneous connection, respectively, which prevent erroneous connection (i.e. inversely connected state) between the abdominal cavity tube 10 and the luminal cavity tube 22.

The abdominal cavity supply fitting 21A and the luminal cavity supply fitting 21B are adapted, for example, to differentiate the outer diameters of the fittings from each other as well as to differentiate the number of projections from each other provided on the outer peripheries of the fittings so as to enable identification of one fitting from the other, thereby preventing erroneous connection.

A connector (hereinafter referred to an abdominal cavity connector) 43 for the abdominal cavity tube 10, which is to be connected to the abdominal cavity supply fitting 21A, and a connector (hereinafter referred to a luminal cavity connector) 44 for the luminal cavity tube 22, which is to be connected to the luminal cavity supply fitting 21B, are configured, respectively, although not shown, to have shapes matched to those of the gas supply fittings.

Figure 6B:
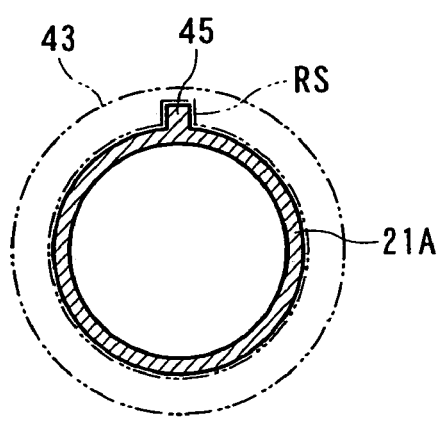
FIG. 6B is a sectional view showing a structure along a direction orthogonal to a longitudinal direction to illustrate a state of connection between an abdominal cavity fitting and a connector for an abdominal cavity tube.

As shown in FIG. 6B, the abdominal cavity supply fitting 21A, for example, has a larger outer diameter than the luminal cavity supply fitting 21B, and is formed to have a single projection 45 at a predetermined position on its outer periphery. Further, the abdominal cavity connector 43 is formed to have an inner diameter, not shown, that matches the outer diameter of the abdominal cavity supply fitting 21A, with a notch (not shown) being provide in its inner peripheral surface to fit with the projection 45. In this way, the abdominal cavity connector 43 is adapted to fit into and connected to the abdominal cavity supply fitting 21A.

Figure 6C:
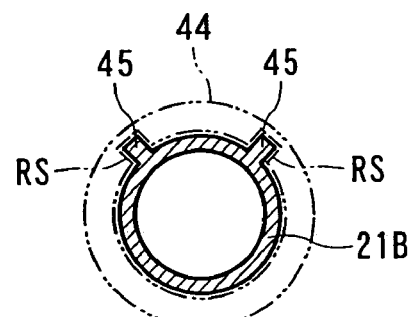
FIG. 6C is a sectional view showing a structure along a direction orthogonal to a longitudinal direction to illustrate a state of connection between a luminal cavity fitting and a connector for a luminal cavity tube.

As shown in FIG. 6C, the luminal cavity supply fitting 21B, for example, has a smaller outer diameter than the abdominal cavity supply fitting 21A, and is formed to have two projections 45 at predetermined positions on its outer periphery. Further, the abdominal cavity connector 44 is formed to have an inner diameter, not shown, that matches the outer diameter of the luminal cavity supply fitting 21B, with two notches (not shown) being provide in its inner peripheral surface to fit with the two projections 45, respectively. In this way, the luminal cavity connector 44 is adapted to fit into and connected to the luminal cavity supply fitting 21B.

It should be noted that, in the present embodiment, the abdominal cavity supply fitting 21A and the luminal cavity supply fitting 21B are so configured to have varied diameter, number of projections or the like for distinction from each other, however, there is no intention of limiting to these variations. For example, as to outer diameters, those of the pair of the supply fitting 21B and the connector 44 for luminal cavity may be configured to be larger than those of the pair of the supply fitting 21A and the connector 43 for abdominal cavity. In addition, the number of projections 45 formed in the outer peripheral surfaces of the abdominal cavity supply fitting 21A and the luminal cavity supply fitting 21B, i.e. the number of recesses RS formed in the inner peripheral surfaces of the abdominal cavity connector 43 and the luminal cavity connector 44, respectively, may not be limited to the number shown in FIGS. 6B and 6C, and thus, for example, three or more projections and recesses may be provided to the luminal cavity supply fitting 21B and the luminal cavity connector 44, respectively.

Further, only the outer diameters of the fittings 21A and 21B, i.e. only the inner diameters of the connectors 44 and 45 may be differentiated from each other between the uses for an abdominal cavity and a luminal cavity, without forming projections or recesses. Alternatively, Sizes and shapes of the fittings and the connectors may be configured to have completely the same between the uses for an abdominal cavity and a luminal cavity, but to have different numbers or shapes of the projections and recesses for distinction from each other.

Furthermore, the fittings and the connectors may be configured to have colored members or the like at the outer peripheries thereof to enable identification from each other.

The effects of the gas supply apparatus 21 of the present embodiment are described below.

In a laparoscopic surgery, an operator is to connect both of the abdominal cavity tube 10 and the luminal cavity tube 22 to the gas supply apparatus 21 in order to give treatment by internally and externally specifying a site to be treated with the insertion of the endoscope 12 into a luminal cavity, such as a large intestine.

On this occasion, as the abdominal cavity supply fitting 21A and the luminal cavity supply fitting 21B, as shown in FIG. 6A, are configured such that the respective diameters are different from each other and that the number of projections provided on the respective peripheries are different from each other, the operator can make a distinction between the abdominal cavity supply fitting 21A and the luminal cavity supply fitting 21B only through visual observation.

In addition, as the abdominal cavity connector 43 and the luminal cavity connector 44 are configured to have shapes that match those of the two supply fittings 21A and 21B, respectively, when the operator erroneously attempt to connect the luminal cavity connector 44 to the abdominal cavity supply fitting 21A, no fitting or connection is obtained. Of course, contrarily, however an operator may attempt to connect the luminal cavity supply fitting 21B to the abdominal cavity connector 43, no fitting or connection is obtained. Thus, erroneous connection can be prevented.

In the gas supply apparatus 21 of the present embodiment, when an operator operates the abdominal cavity instruction button 21k, the luminal cavity instruction button 21m and the gas supply start button 21b, carbon dioxide gas having a pressure suitable for an abdominal cavity is supplied, as described above, to the abdominal cavity supply fitting 21A under the control of the controller 40 over the first electropneumatic proportional valve 33, and similarly, carbon dioxide gas having a pressure suitable for a luminal cavity is supplied to the luminal cavity supply fitting 21B under the control of the controller 40 over the second electropneumatic proportional valve 34. In short, gas supply with right pressure is effected to the abdominal cavity supply fitting 21A and the luminal cavity supply fitting 21B.

Thus, according to the present embodiment, effective utilization of a space can be achieved by allowing the gas supply apparatus 21 to have a function of a conventional abdominal insufflation apparatus and a function of an ECR.

In addition, as the abdominal cavity supply fitting 21A and the luminal cavity supply fitting 21B are provided in juxtaposition in the integrated front panel FP of the gas supply apparatus 21, connecting operation can be performed in shorter time and in a smoother manner than a conventional system wherein connectors have to be connected to gas supply fittings that are provided in separate devices, respectively, and thus less erroneous connections come to occur. This correct tube connection for inflating both an abdominal cavity and a luminal cavity by simultaneously supplying carbon dioxide gas therein may ensure sufficient visual fields for the endoscopes 5 and 12, and treatment tools (not shown), respectively.

Further, in the gas supply apparatus 21 of the present embodiment, means for preventing erroneous connection in connecting the abdominal cavity supply fitting 21A and the luminal cavity supply fitting 21B to the abdominal cavity connector 43 and the luminal cavity connector 44, respectively, are positively established. Therefore, erroneous connection of the connectors can be prevented, and hence carbon dioxide gas may be supplied at right gas supply pressures through these two abdominal cavity supply fitting 21A and the luminal cavity supply fitting 21B, respectively.

Second Embodiment

An endoscopic system in which a second embodiment of a gas supply apparatus of the present invention is implemented, is described with reference to FIGS. 7 to 9. Note that in this embodiment, the same or like functional effects are referred to by the same reference numbers to omit or simplify the description. The manner of omission and simplification is applied to a third and the subsequent embodiments.

The gas supply apparatus 21 of the present embodiment provides the abdominal cavity supply fitting 21A and the luminal cavity supply fitting 21B both having entirely the same size, but is different from the first embodiment in that a connecting state is electrically detected and that a gas supply to the two supply fittings 21A and 21B is controlled depending on the results of the detection.

Figure 7A:
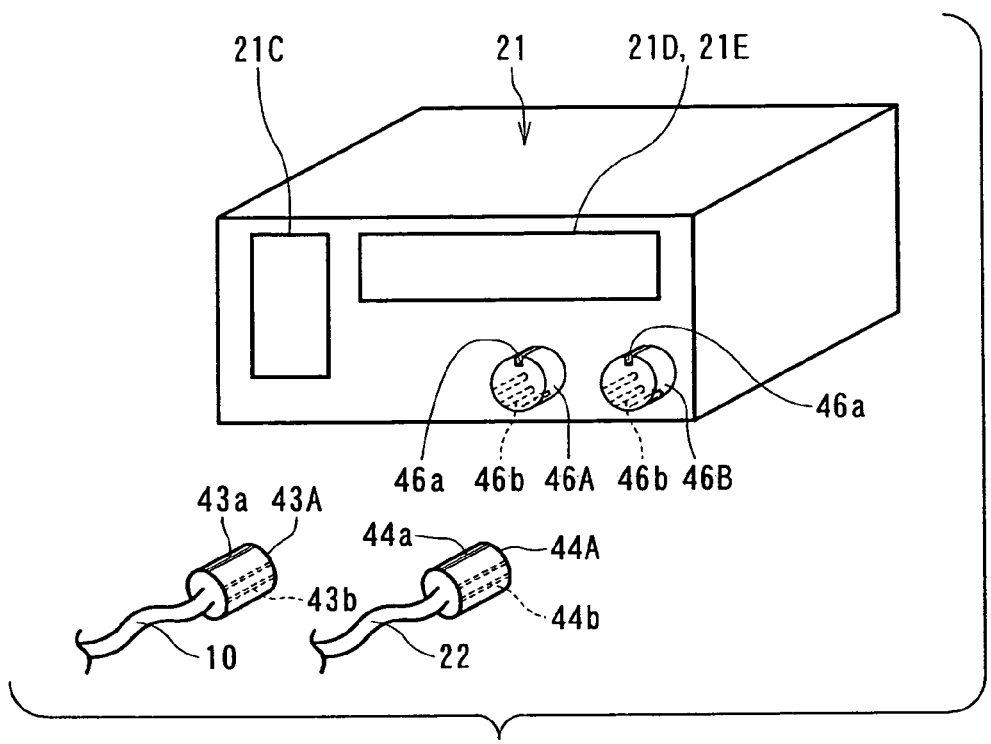
FIG. 7A is a perspective view of a front panel of a gas supply device mounting gas supply fittings, and an abdominal cavity tube and a luminal cavity tube to be connected to the gas supply fittings, respectively, according to a second embodiment of the gas supply apparatus of the present invention.

As shown in FIG. 7A, the front panel FP of the gas supply apparatus 21 of the present embodiment is provided with an abdominal cavity supply fitting 46A and a luminal cavity supply fitting 46B of approximately the same shape (the same diameter), each having three electrical contacts 46b which are formed on a respective outer peripheral surface.

Figure 7B:
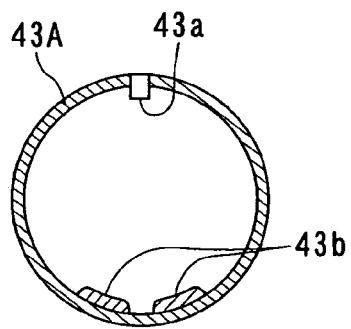
FIG. 7B is a sectional view showing a structure along a direction orthogonal to a longitudinal direction of a connector for an abdominal cavity tube.
Figure 7C:
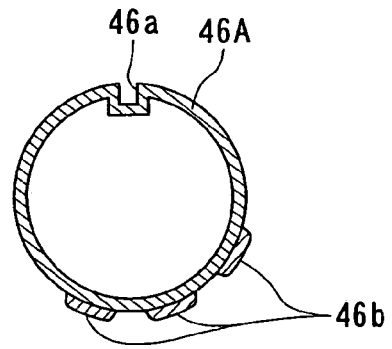
FIG. 7C is a sectional view showing a structure along a direction orthogonal to a longitudinal direction of a connector for a luminal cavity tube.
Figure 7D:
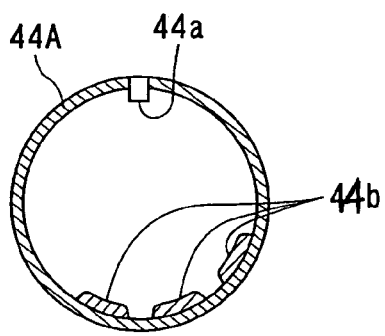
FIG. 7D is a sectional view showing a structure along a direction orthogonal to a longitudinal direction of a supply fitting for an abdominal cavity.
Figure 7E:
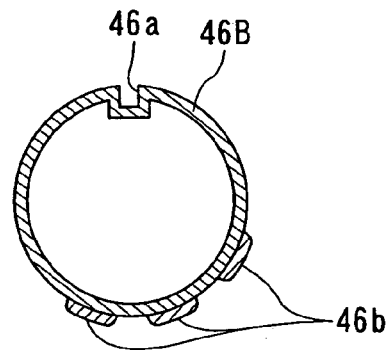
FIG. 7E is a sectional view showing a structure along a direction orthogonal to a longitudinal direction of a supply fitting for a luminal cavity.

Each of these electrical contacts 46b consists of a pair of conductive electrical pieces. For the present embodiment, as shown in FIGS. 7C and 7E, three electrical contacts 46b are formed, by way of example, at each of the abdominal cavity supply fitting 46A and the luminal cavity supply fitting 46B. In addition, a positioning groove 46a is provided at a portion on an outer peripheral surface of each of the abdominal cavity fitting 46A and the luminal cavity supply fitting 46B.

An abdominal cavity connector 43A and a luminal cavity connector 44A are configured to have a shape that fits into the two supply fittings 46A and 46B, respectively. The abdominal cavity connector 43A and the luminal cavity connector 44A are configured to have electrical contacts 43b, on inner peripheries thereof, which are to be electrically in contact with the electrical contacts 46b, respectively. The electrical contacts 43b are comprised, for example, of a conductive material. For the present embodiment, as shown in FIG. 7B, two electrical contacts 43b are formed, by way of example, at the abdominal cavity connector 43A. In addition, as shown in FIG. 7D, three electrical contacts 43b are formed, by way of example, at the luminal cavity connector 44A. Further, the abdominal cavity connector 43A and the luminal cavity connector 44A are configured to have positioning projections 43a and 44a, at a predetermined position in inner peripheral surfaces thereof, respectively, to fit into the positioning grooves 46a, respectively, and to be in position.

Specifically, as shown in FIG. 7B, two electrical contacts 43b are disposed at predetermined positions at a lower inner peripheral surface of the abdominal cavity connector 43A. The abdominal cavity supply fitting 46A, as shown in FIG. 7C, to which the abdominal cavity connector 43A is fitted is provided with three electrical contacts 46b.

It is configured such that, in fitting the abdominal cavity connector 43A into the abdominal cavity supply fitting 46A for connection, the positioning projection 43a is engaged with the positioning groove 46a to ensure electrical contact between the two electrical contacts 43b and the two electrical contacts 46b, respectively.

Figure 8:
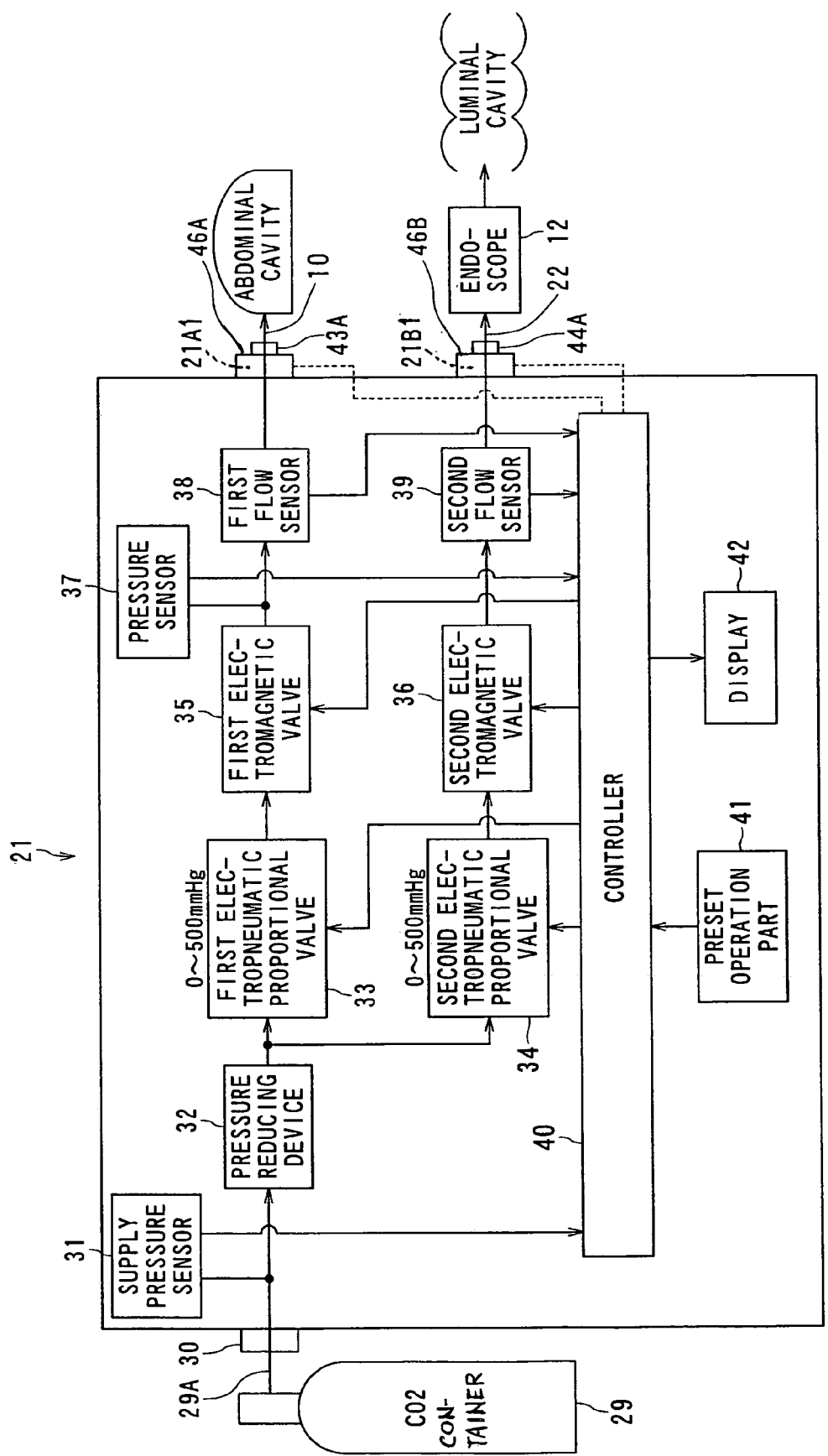
FIG. 8 is a block diagram illustrating a configuration of a second embodiment of a gas supply apparatus of the present invention.

Further, the electrical contacts 46b of the abdominal cavity supply fitting 46A and the electrical contacts 43b of the abdominal cavity connector 43A form a first detector 21A1 as a sensor (see FIG. 8).

The respective electrical contacts 46b of the fitting 46A are connected to the controller 40 and are applied current from the controller 40 at the time connection is judged. Therefore, when the contacts 46b and 43b are, respectively, in contact with each other, the controller 40 may obtain an electrical signal indicative of normality of connection in response to such a current application. Specifically, for the present embodiment, the controller 40 judges as to whether or not the connection is in normality wherein electrical signals indicative of connection are obtained from the two of the three electrical contacts 46b, which are in predetermined positions, provided at the abdominal cavity supply fitting 46A. This may allow the first detector 21A1 to function as a sensor for detecting a state of connection between the abdominal cavity supply fitting 46A and the abdominal cavity connector 43A. Briefly, the controller 40 can obtain information as to whether or not the fitting and the connector are appropriately in electrical connection with each other.

Contrarily, where connection is out of the above described normality (i.e. when signals indicative of contact is obtained from one or three of the three electrical contacts 46b of the abdominal cavity supply fitting 46A, or when no signal indicative of contact is obtained from any of the contacts 46b), the controller 40 can obtain electrical signals indicative of abnormality of connection (erroneous connection).

In short, as shown in FIG. 8, the first detector 21A1 may function as a sensor for detecting a state of connection between the connector and the fitting, and may give information to the controller 40 as to whether or not the two of the electrical contacts 43b and two electrical contacts 46b, respectively, are appropriately in electrical contact with each other.

As shown in FIG. 7D, three electrical contacts 43b are disposed at predetermined positions at a lower inner peripheral surface of the luminal cavity connector 44A.

The luminal cavity supply fitting 46B to fit into the luminal cavity connector 44A is provided, as shown in FIG. 7E, with three electrical contacts 46b at predetermined positions on an outer peripheral surface so as to be electrically connected to the three electrical contacts 43b, respectively, of the luminal cavity connector 44A.

It is configured such that, in fitting the luminal cavity connector 44A to the luminal cavity supply fitting 46B for connection, the positioning projection 44a is engaged with the positioning groove 46a to ensure electrical connection between the three electrical contacts 43b and the three electrical contacts 46b, respectively, as described hereinbefore.

The electrical contacts 46b of the luminal cavity supply fitting 46B and the electrical contacts 43b of the luminal cavity connector 44A form a second detector 21A2 as a sensor (see FIG. 8). The respective electrical contacts 46b of the fitting 46B are connected to the controller 40 and are applied current at the time connection is judged.

Therefore, when both of the contacts 46b and 43b are, respectively, in contact with each other, the controller 40 can obtain an electrical signal indicative of normality of connection in response to such a current application. Specifically, for the present embodiment, the controller 40 judges as to whether or not the connection is in normality wherein electrical signals indicative of connection are obtained from all of the three of the three electrical contacts 46b provided at the luminal cavity supply fitting 46B. This may allow the second detector 21A2 to function as a sensor for detecting a state of connection between the luminal cavity supply fitting 46B and the luminal cavity connector 44A. Briefly, the controller 40 can obtain information as to whether or not the fitting and the connector are in appropriately in electrical connection with each other.

Contrarily, when only portions of both of the contacts 46b and 43b, respectively, are apart from each other, the controller 40 can obtain electrical signals indicative of abnormality of connection (erroneous connection).

In short, as shown in FIG. 8, the second detector 21A2 may function as a sensor for detecting a state of connection between the connector and the fitting, and may give information to the controller 40 as to whether or not the three of the electrical contacts 43b and 46b, respectively, are appropriately electrically connected with each other.

Other portions of the configuration are the same as or equivalent to those of the first embodiment.

Next, effects of the gas supply apparatus 21 of the present embodiment are described.

An operator is supposed to fit the abdominal cavity connector 43A into the abdominal cavity supply fitting 46A for connection. In this instance, the two electrical contacts 43b are reliably connected to the two electrical contacts 46b, respectively, by allowing the positioning projection 43a to engage with the positioning groove 46a.

Also, an operator is supposed to fit the luminal cavity connector 44A into the luminal cavity supply fitting 46B for connection. In this instance, the three electrical contacts 43b are reliably connected to the three electrical contacts 46b, respectively, by allowing the positioning projection 44a to engage with the positioning groove 46a.

Figure 9:
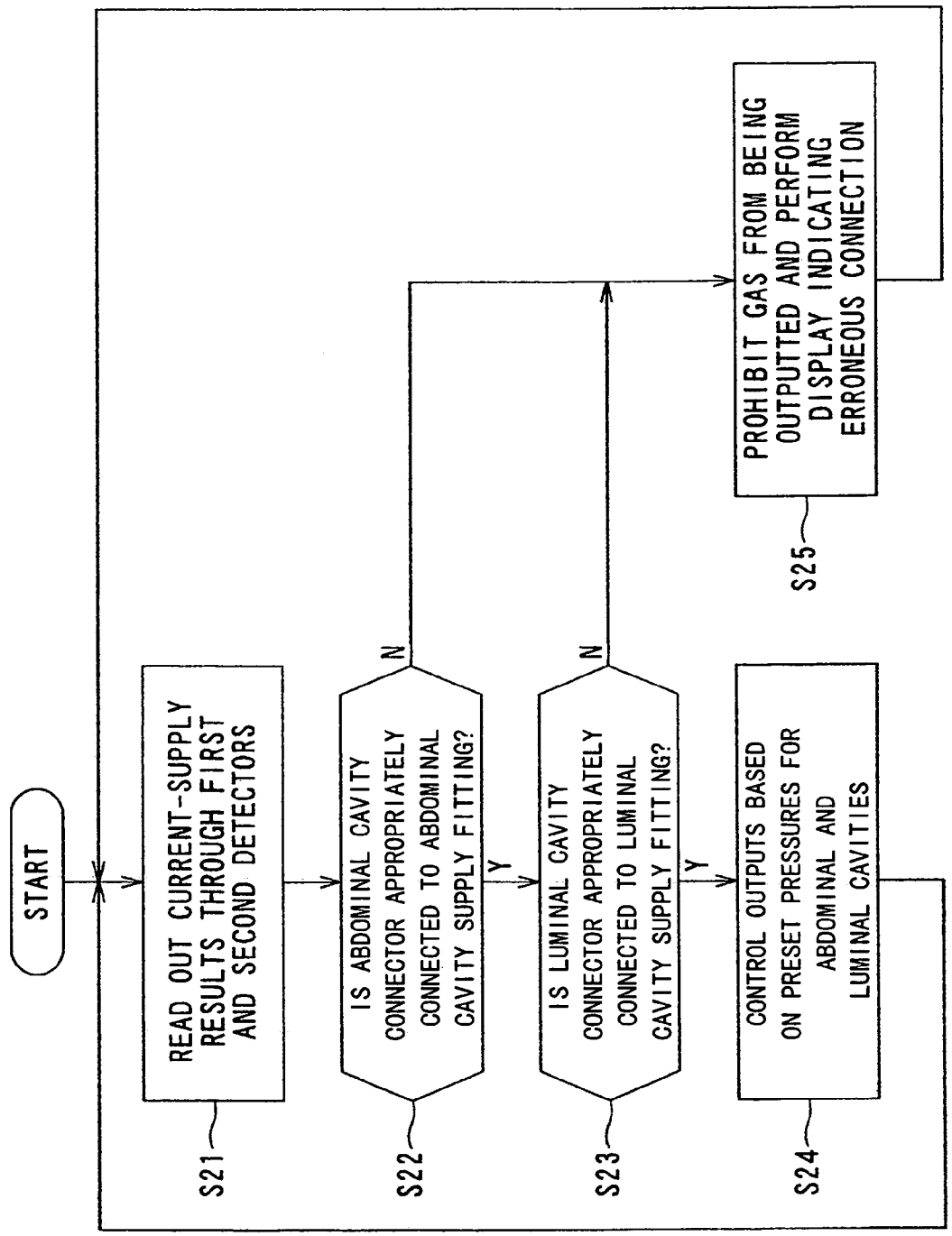
FIG. 9 is a flowchart generally illustrating processes for making judgment of erroneous connection of a tube and for controlling gas supply based on the judgment, which are executed by a controller, according to the second embodiment.

The controller 40 applies current to the first detector 21A1 and the second detector 21A2 to read out the results of the current application (step S21 of FIG. 9). As a result of this current application, when the connector 43A (44A) is correctly connected to the fitting 46A (46B), a signal having a "0" potential, for example, may be obtained as the electrical contacts 43b and 46b are brought into electrical conduction with each other. In contrast, when connection is in error, a signal of potential "1", for example, may be obtained as the electrical contacts 43b and 46b are partially not in conduction with each other.

Then, the controller 40 makes a judgment on whether or not the abdominal cavity connector 43A is appropriately connected to the abdominal cavity supply fitting 46A (step S22). Further, a judgment is also made as to whether or not the luminal cavity connector 44A is appropriately connected to the luminal cavity supply fitting 46B (step S23). It should be noted that the term "appropriately" in these judgment does not include a case where a state of connection is correct, i.e. not inverted, but "inappropriate (incomplete)", such as a case where insertion is insufficient.

When both of the judgments at the steps S22 and S23 are to proceed to YES, i.e. when both of the connectors 43A and 44A are judged to be appropriately connected to both of the fittings 46A and 46B, respectively, the controller 40 permits the first electropneumatic proportional valve 33 and the second electropneumatic proportional valve 34 to effect pressure control (step S24). Thus, the first electropneumatic proportional valve 33 effects valve control so that its discharge pressure will be a pressure suitable for an abdominal cavity. Also, the second electropneumatic proportional valve 34 effects valve control so that its discharge pressure will be a pressure suitable for a luminal cavity.

When an operator has erroneously fit the luminal cavity connector 44A to the abdominal cavity supply fitting 46A, as the three electrical contacts 46b should then all be in a contacted state, the controller 40 may obtains the results of detection as not having been electrically connected from the first detector 21A1 (NO at step S22). Thus, the controller 40, judging that erroneous connection has occurred, controls the first electropneumatic proportional valve 33 and the first electromagnetic valve 35 so as not to effect a gas supply output, and at the same time allows such a gas-supply-stop indication on the front panel FP, such as by flickering a lamp thereon, not shown, for example (step S25).

Further, when an operator has erroneously fit the abdominal cavity connector 43A to the luminal cavity supply fitting 46B, as no complete electrical contact is attained with the three electrical contacts 43b, the controller 40 may also obtain the results of detection as not having been electrically connected from the second detector 21A1 (No at step S23). Thus, the controller 40 makes a judgment of erroneous connection as having been made, and controls the second electropneumatic proportional valve 34 and the second electromagnetic valve 36 so as not to effect a gas supply output.

Thus, according to the present embodiment, similar effects as in the first embodiment can be obtained. Specifically, when the abdominal cavity tube 10 and/or the luminal cavity tube 22 are erroneously connected to the supply fitting 46B and/or 46A, the fact of erroneous connection is automatically and reliably detected to automatically stop a supply of carbon dioxide gas at an inappropriate pressure to the supply fitting 46A and/or 46B.

Therefore, an operator is obliged to reconnect the tube 10 (22) to the right fitting 46A (46B), and when such a reconnection is suitably done, an allowance is made to supply carbon dioxide gas to the supply fitting 46A and/or 46B at an appropriate pressure.

In this way, according to the present embodiment, a configuration, in which the abdominal cavity supply fitting 46A and the luminal cavity supply fitting 46B have a similar shape, cannot result in erroneous connection but enables a supply of carbon dioxide gas at a right pressure to the respective two supply fittings 46A and 46B. The common diameter and the shape between the fittings 46A and 46B are advantageous from a viewpoint of manufacturing cost.

Third Embodiment

An endoscopic system in which a third embodiment of the gas supply apparatus of the present invention is implemented is described with reference to FIGS. 10A to 10D and 11.

The present embodiment is an improvement of the gas supply apparatus 21 of the second embodiment, which is different from the second embodiment in that the present embodiment is configured such that distinction between an abdominal and luminal cavity connectors is made not based on contact/noncontact between the electrical contacts, but based on the results of detection of an internal resistance at the electrical contacts.

Figure 10A:
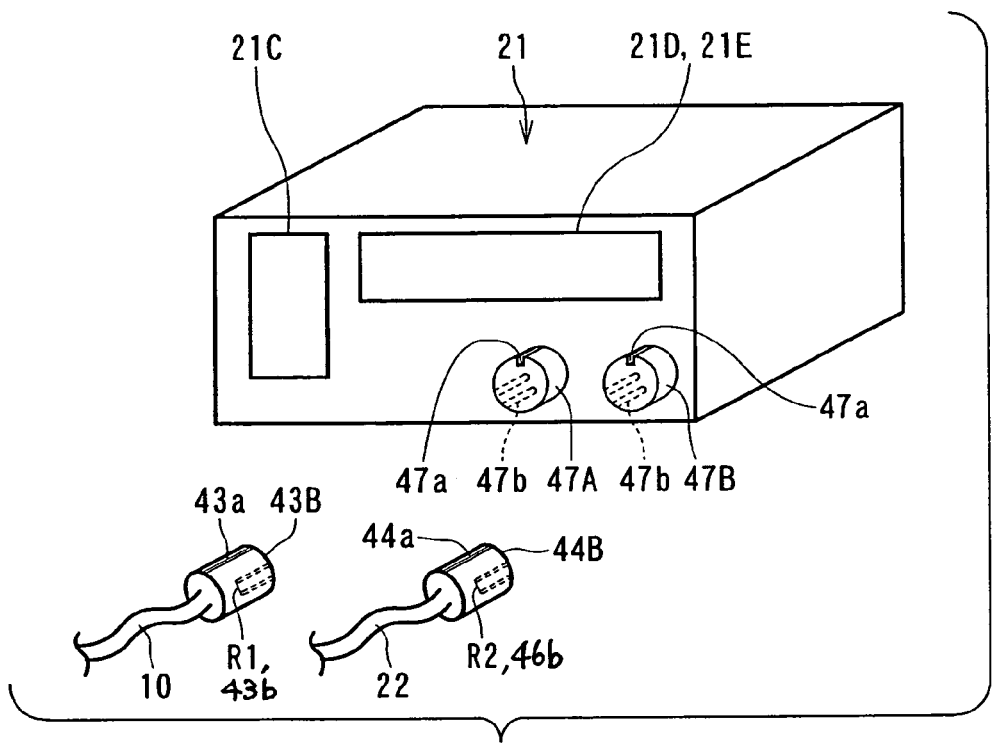
FIG. 10A is a perspective view of a front panel of a gas supply apparatus mounting gas supply fittings, and an abdominal cavity tube and a luminal cavity tube to be connected to the gas supply fittings, respectively, according to a third embodiment of the gas supply apparatus of the present invention.
Figure 10B:
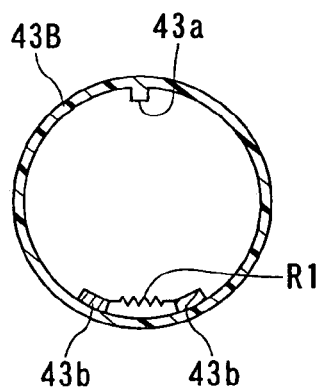
FIG. 10B is a sectional view showing a structure along a direction orthogonal to a longitudinal direction of a connector for of an abdominal cavity tube.
Figure 10C:
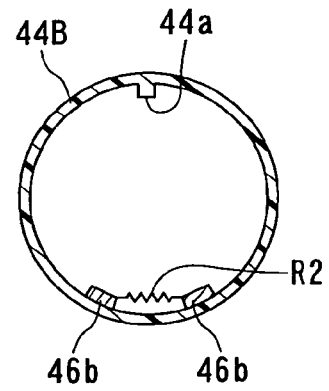
FIG. 10C is a sectional view showing a structure along a direction orthogonal to a longitudinal direction of a connector for a luminal cavity tube.
Figure 10D:
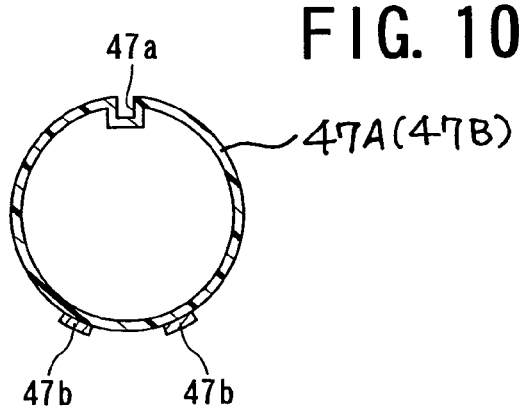
FIG. 10D is a sectional view showing a structure along a direction orthogonal to a longitudinal direction of a supply fitting for an abdominal cavity or a supply fitting for a luminal cavity.

As shown in FIGS. 10A and 10D, the gas supply apparatus 21 of the present embodiment is provided with an abdominal cavity supply fitting 47A and a luminal cavity supply fitting 47B having the same shape (the same diameter), which is approximately the same as the second embodiment. Each of the abdominal cavity supply fitting 47A and the luminal cavity supply fitting 47B has two electrical contacts 47b on an outer peripheral surface thereof.

An abdominal cavity connector 43B and a luminal cavity connector 44B are configured so as to have shapes that fit into the two supply fittings 46A and 46B, respectively, which is approximately the same as the second embodiment. The abdominal cavity connector 43B and the luminal cavity connector 44B are configured so as to have two electrical contacts 43b and two electrical contacts 46b, respectively, at positions on respective inner peripheral surfaces thereof, which match the positions of the electrical contacts 47b for electrical connection therebetween.

As shown in FIG. 10B, the abdominal cavity connector 43B has, at the two electrical contacts 43b, a resistance which is equivalent to a resistor R1. The resistance of the resistor R1 is an internal resistance of the electrical contacts 43b.

As shown in FIG. 10C, the luminal cavity connector 44B has, at the two electrical contacts 46b, a resistance which is equivalent to a resistor R2. The resistance of the resistor R2 is an internal resistance of the electrical contacts 46b. In the present embodiment, the resistances of the resistor R1 and the resistor R2 are not the same but are predetermined different resistances which are adapted to be recorded on a memory, not shown, in the controller 40.

In the present embodiment, it is configured that, when the abdominal cavity connector 43B is fit into the abdominal cavity supply fitting 47A for connection, a positioning projection 43a is brought into engagement with a positioning groove 47a, by which the two electrical contacts 43b are reliably electrically connected to the two electrical contacts 47b, respectively.

Also, it is configured that, when the luminal cavity connector 44B is fit into the luminal cavity supply fitting 47B for connection, a positioning projection 44a is brought into engagement with the positioning groove 47a, in the like manner as described above, by which the two electrical contacts 46b are reliably electrically connected to the two electrical contacts 47b, respectively.

Further, the electrical contacts 47b of the abdominal cavity supply fitting 47A and the electrical contacts 47b of the luminal cavity supply fitting 47B are configured to be connected to the controller 40, as in the second embodiment, so as to be charged with electricity from the controller 40 at the time of judging connection.

Thus, the two electrical contacts 47b of the abdominal cavity supply fitting 47A and the two electrical contacts 43b (resistor R1) of the abdominal cavity connector 43B constitute a first detector 21A1 as a sensor. Also, the two electrical contacts 47b of the luminal cavity supply fitting 47B and the two electrical contacts 46b (resistor R2) of the luminal cavity connector 44B constitute a second detector 21A2 as a sensor (see FIG. 8 as described hereinbefore).

Other portions of the configuration are similar to those of the second embodiment.

In the present embodiment, a description has been given of a configuration in which are provided two electrical contacts 43b and two electrical contacts 47b for an abdominal cavity side, and two electrical contacts 46b and two electrical contacts 47b for a luminal cavity side. However, without limitation to this, other configuration may be provided in which at least one electrical contact is provided each at an abdominal cavity side and a luminal cavity side, and resistors R1 and R2 of different resistances are provided at the connector side electrical contacts, respectively.

Next, effects of the gas supply apparatus 21 of the present embodiment are described with reference to FIG. 11.

In a laparoscopic surgery, an operator is to connect the abdominal cavity tube 10 and the luminal cavity tube 22 to the gas supply apparatus 21 in order to give treatment by inserting the endoscope 12 into a luminal cavity, such as a large intestine for internal and external specification of a site to be treated.

At this time, assuming that the gas supply apparatus 21 is switched on, the controller 40 starts a program shown in FIG. 11.

The controller 40 charges electricity to the first detector 21A1 and the second detector 21B1 through a process at step S1, by which each of the resistances of the resistors R1 and R2 of the connected connectors (the abdominal cavity connector 43B and the luminal cavity connector 44B) is detected (measured).

Thereafter, the controller 40 makes a judgment, through a judgment process at step S2, as to whether or not the resistance detected by the first detector 21A1 is the same as a resistance of the resistor R1 of the abdominal cavity connector 43B.

In case the detected resistance is judged to be the same as the resistance of the resistor R1 of the abdominal cavity connector 43B, the controller 40 allows processes to proceed to step S3. Contrarily, in case a judgment is made as being different, erroneous connection is regarded to have occurred at step S5, which is then informed to an operator by lighting up an erroneous connection indicator, not shown, of the display 42. At the same time, the first electropneumatic proportional valve 33 and the first electromagnetic valve 35 are controlled so as to stop supply of carbon dioxide gas, and then processes are allowed to return to step S1.

In the judgment process at step S3, the controller 40 judges on whether or not the resistance detected by the second detector 21B1 is the same as the resistance of the resistor R2 of the luminal cavity connector 44B.

In case the detected resistance is judged to be the same as the resistance of the resistor R2 of the abdominal cavity connector 44B, the controller 40 allows processes to proceed to step S4. Contrarily, in case a judgment is made as being different, processes are allowed to proceed to step S5 to carry out processing of indication in this regard and of stopping gas supply output, as described above, and then processes are allowed to return to step S1.

The controller 40 then controls, in the process at step S4, the first electropneumatic proportional valve 33 so that carbon dioxide gas having a pressure suitable for an abdominal cavity is supplied to the abdominal cavity supply fitting 47A, and at the same time, controls the second electropneumatic proportional valve 34 so that carbon dioxide gas having a pressure suitable for a luminal cavity is supplied to the luminal cavity supply fitting 47B. Then, the controller 40 allows processes to return to step S1 being ready for next connection of connectors.

Thus, according to the present embodiment, when the abdominal cavity supply fitting 47A and the luminal cavity supply fitting 47B are configured to have the same shape, erroneous connection is ultimately prevented as in the second embodiment, and carbon dioxide gas is allowed to be supplied to the respective two supply fittings 47A and 47B with right pressures.

Fourth Embodiment

An endoscopic system in which a fourth embodiment of the gas supply apparatus of the present invention is implemented is described with reference to FIG. 12. It should be noted that in FIG. 12, like processing contents as the ones shown in FIG. 11 of the third embodiment are referenced by the same step number.

In the present embodiment, the gas supply apparatus 21 is approximately the same as the one in the third embodiment except that the present embodiment is configured such that the controller 40 performs automatic control by detecting internal resistances at electrical contacts, judging on connections of luminal cavity and abdominal cavity connectors based on the results of the detection, and supplying gas at optimal predetermined pressures depending on the type of connected connectors based on the results of the judgment.

Other portions of the configuration of the gas supply apparatus 21 are similar to those of the second embodiment.

Effects of the gas supply apparatus 21 of the present embodiment are described with reference to FIG. 12.

In a laparoscopic surgery, an operator is to connect the abdominal cavity tube 10 and the luminal cavity tube 22 to the gas supply apparatus 21 in order to give treatment by inserting the endoscope 12 to a luminal cavity, such as a large intestine for internal and external specification of a site to be treated.

At this time, assuming that the gas supply apparatus 21 is switched on, the controller 40 starts the program shown in FIG. 12.

Then, in the process at step S1, the controller 40 detects (measures), via the first detector 21A1 and the second detector 21B1, respective resistances of the resistors R1 and R2 of the connectors (the abdominal cavity connector 43B and the luminal cavity connector 44B) connected to the fittings 47A and 47B, respectively.

Thereafter, the controller 40 makes a judgment, in the process at step S2, on whether or not the resistance detected by the first detector 21A1 is the same as the resistance of the resistor R1 of the abdominal cavity connector 43B.

In case the detected resistance is judged to be the same as the resistance of the resistor R1 of the abdominal cavity connector 43B, the controller 40 allows processes to proceed to step S10. Contrarily, in case a judgment is made as being different, processes are allowed to proceed to step S11.

At step S10, the controller 40 sets a pressure value for abdominal cavity to be used for supplying carbon dioxide gas of a pressure suitable for an abdominal cavity to the abdominal cavity supply fitting 47A, and at the same time, controls the first electropneumatic proportional valve 33 based on the set pressure value for abdominal cavity, and then processes are allowed to proceed to step S3.

In a judgment process at step S11, the controller 40 judges as to whether or not the resistance detected by the first detector 21A1 is the same as the resistance of the resistor R2 of the luminal cavity connector 44B. In case the detected resistance is judged to be the same as the resistance of the resistor R2 of the luminal cavity connector 44B, the controller 40 judges the luminal cavity connector 44B as having been connected to the abdominal cavity supply fitting 47A. Then, in a process at step S12, a pressure value for a luminal cavity is set to supply carbon dioxide gas of a pressure suitable for the luminal cavity from the abdominal cavity supply fitting 47A, and based on the set pressure for a luminal cavity, the first electropneumatic proportional valve 33 is controlled. After that, processes are allowed to proceed to step S3. If the resistance is judged not to be the same in a judgment process at step S11, processes are, as well, allowed to return to step S3.

In the judgment process at step S3, the controller 40 makes a judgment as to whether or not the resistance detected by the second detector 21B1 is the same as the resistance of the resistor R2 of the luminal cavity connector 44B.

When the detected resistance is judged to be the same as the resistance of the resistor R2 of the luminal cavity connector 44B, the controller 40 allows processes to proceed to step S13, and when the resistance is judged as not being the same, processes are allowed to proceed to step S14.

At step S13, the controller 40 sets a pressure value for a luminal cavity to supply carbon dioxide gas of a pressure suitable for a luminal cavity to the luminal cavity supply fitting 47B, and at the same time, controls the second electropneumatic proportional valve 34 based on the set pressure value for a luminal cavity, and then processes are allowed to return to steps S1.

In a judgment process at step S14, the controller 40 judges on whether or not the resistance detected by the second detector 21B1 is the same as the resistance of the resistor R1 of the abdominal cavity connector 43B. In case the detected resistance is judged to be the same as the resistance of the resistor R1 of the abdominal cavity connector 43B, the controller 40 judges the abdominal cavity connector 43B as having been connected to the luminal cavity supply fitting 47B. Then, in a process at step S15, the controller 40 sets a pressure value for an abdominal cavity to supply carbon dioxide gas of a pressure suitable for an abdominal cavity from the luminal cavity supply fitting 47B, and controls the second electropneumatic proportional valve 34 based on the set pressure value for an abdominal cavity. Thereafter, processes are allowed to return to step S1. Meanwhile, in case a judgment is made as not being the same, processes are, as well, allowed to return to step S1.

Thus, even when a wrong connector has been erroneously connected to the abdominal cavity supply fitting 47A and the luminal cavity supply fitting 47B, gas supply can be performed with a right pressure via the abdominal cavity supply fitting 47A and the luminal cavity supply fitting 47B, depending on the abdominal cavity connector 43B or the luminal cavity connector 44B that has been connected.

Thus, according to the present embodiment, irrespective of the occurrences of erroneous connection, the abdominal cavity connector 43B and the luminal cavity connector 44B are automatically identified, and based on the results of the identification, gas supply can be carried out with a right pressure. Such an automatic control enables automatic gas supply, even when an abdominal cavity side gas supply conduit or a luminal cavity side gas supply conduit breaks down, at an optimum pressure for an abdominal cavity or a luminal cavity through a supply fitting which is in order, thereby allowing an operation to proceed without interruption.

The gas supply apparatus of each of the embodiments described above is configured such that an abdominal cavity supply fitting and a luminal cavity supply fitting are integrally provided and that carbon dioxide gas can be supplied at a right pressure through respective supply fittings, and accordingly that the space of an operating room can be effectively utilized. The gas supply apparatus of each of the embodiments is especially effective in a laparoscopic surgery wherein treatment is given by inserting an endoscope into a luminal cavity for internal and external specification of a site to be treated.

The present invention is not limited to the first to fourth embodiments described above, but may be embodied in many other ways with various modulations without departing from the scope of the invention. Additionally, the embodiments described above include inventions at various stages, and thus suitable combinations of the disclosed plurality of components may extract various inventions.

What is claimed is:

1. A gas supply apparatus comprising:
a first fitting through which a gas of a first pressure is discharged;
a second fitting through which a gas of a second pressure is discharged;
a first tube having one end to which a first connector connectable to the first fitting is attached and supplying the gas of the first pressure to a first body cavity of a subject to be medically treated;
a second tube having one end to which a second connector connectable to the second fitting is attached and supplying the gas of the second pressure to a second body cavity of the subject;
a single gas source supplying a gas used for supply of the gas of the first and second pressures;
a gas supply unit controlling the gas supplied from the gas source to provide both of the first and second fittings with both of the gases of the first and second pressures, respectively;
a sensor detecting information indicative of a condition of the first connector connected to the first fitting and information indicative of a condition of the second connector connected to the second fitting;
a determination unit determining whether or not the first connector is correctly connected to the first fitting, determining whether or not the second connector is correctly connected to the second fitting, determining whether or not the second connector is connected to the first fitting when determining that the first connector is not connected to the first fitting, and determining whether or not the first connector is connected to the second fitting when determining that the second connector is not connected to the second fitting, based on the information from the sensor; and
a gas supply control unit controlling, based on a result determined by the determination unit, the gas supply unit to supply the gas of the first pressure and the gas of the second pressure; wherein when the determination unit determines that the first connector is correctly connected to the first fitting, the gas supply control unit controls the gas supply unit to supply the gas of the first pressure to the first fitting, when the determination unit determines that the second connector is correctly connected to the second fitting, the gas supply control unit controls the gas supply unit to supply the gas of the second pressure to the second fitting, when the determination unit determines that the second connector is connected to the first fitting, the gas supply control unit controls the gas supply unit to supply the gas of the second pressure to the first fitting, and when the determination unit determines that the first connector is connected to the second fitting, the gas supply control unit controls the gas supply unit to supply the gas of the first pressure to the second fitting.

2. The gas supply apparatus according to claim 1, wherein both of the first and second fittings are formed on a surface of a casing of the gas supply apparatus, whereby an operator manually operates to connect both of the first and second connectors to both of the first and second fittings, respectively.

3. The gas supply apparatus according to claim 1, wherein the gas supply control unit issues a command to allow the gas of the first pressure to be supplied to the first fitting in a case where the determination unit determines that the first connector is correctly connected to the first fitting, issues a command to prohibit the gas of the first pressure from being supplied to the first fitting in a case where the determination unit determines that the first connector is not connected to the first fitting, issues a command to allow the gas of the second pressure to be supplied to the second fitting in a case where the determination unit determines that the second connector is correctly connected to the second fitting, issues a command to prohibit the gas of the second pressure from being supplied to the second fitting in a case where the determination unit determines that the second connector is not connected to the second fitting;

issues a command to allow the gas of the second pressure to be supplied to the first fitting in a case where the determination unit determines that the second connector is connected to the first fitting, and issues a command to allow the gas of the first pressure to be supplied to the second fitting in a case where the determination unit determines that the first connector is connected to the second fitting.

4. The gas supply apparatus according to claim 3, further comprising a display unit informing an erroneous connection when the determination unit determines that the first connector is not connected to the first fitting or the second connector is not connected to the second fitting.

5. The gas supply apparatus according to claim 1, wherein the sensor includes a resistor with conductive contact portions at both ends thereof arranged on either the first fitting or the first connector and on the second fitting or the second connector, respectively; and conductive contact portions arranged on the remaining one of the first fitting and the first connector and on the remaining one of the second fitting and the second connector, respectively, and allowed to touch the contact portions of the resistor when being connected, and the determination unit performs the determination, at each of the first and second fittings, on the basis of results obtained when current is made to flow through the resistor via the contact portions on both the first and second fittings and the first and second connectors.

6. The gas supply apparatus according to claim 5, further comprising positioning means for positioning both the first connector connected to the first fitting and the second connector connected to the second fitting.

7. A method of managing connections of tubes arranged in a gas supply apparatus, comprising steps of:

detecting a connected condition of a first tube connected to a first fitting through which a gas of a first pressure is discharged;

detecting a connected condition of a second tube connected to a second fitting through which a gas of a second pressure is discharged;

determining whether or not the first connector is correctly connected to the first fitting;

determining whether or not the second connector is correctly connected to the second fitting;

determining whether or not the second connector is connected to the first fitting when determining that the first connector is not connected to the first fitting;

determining whether or not the first connector is connected to the second fitting when determining that the second connector is not connected to the second fitting;

issuing a command to allow the gas of the first pressure to be supplied to the first fitting in a case where it is determined that the first connector is correctly connected to the first fitting, while issuing a command to prohibit the gas of the first pressure from being supplied to the first fitting in a case where it is determined that the first connector is not connected to the first fitting;

issuing a command to allow the gas of the second pressure to be supplied to the second fitting in a case where it is determined that the second connector is correctly connected to the second fitting, while issuing a command to prohibit the gas of the second pressure from being supplied to the second fitting in a case where it is determined that the second connector is not connected to the second fitting;

issuing a command to allow the gas of the second pressure to be supplied to the first fitting in a case where it is determined that the second connector is connected to the first fitting; and issuing a command to allow the gas of the first pressure to be supplied to the second fitting in a case where it is determined that the first connector is connected to the second fitting.

8. The managing method according to claim 7, further comprising a step of performing display notifying an erroneous connection when it is determined that the first connector is not connected to the first fitting or the second connector is not connected to the second fitting.

* * * * *